US009163070B2

(12) United States Patent
Baumann

(10) Patent No.: US 9,163,070 B2
(45) Date of Patent: Oct. 20, 2015

(54) DESIGNED ANKYRIN REPEAT PROTEINS BINDING TO PLATELET-DERIVED GROWTH FACTOR

(71) Applicant: MOLECULAR PARTNERS AG, Schlieren (CH)

(72) Inventor: Michael Baumann, Winterthur (CH)

(73) Assignee: MOLECULAR PARTNERS AG, Schlieren (CH)

( * ) Notice: Subject to any disclaimer, the term of this patent is extended or adjusted under 35 U.S.C. 154(b) by 0 days.

(21) Appl. No.: 13/928,973

(22) Filed: Jun. 27, 2013

(65) Prior Publication Data
US 2014/0005125 A1    Jan. 2, 2014

(30) Foreign Application Priority Data

Jun. 28, 2012 (EP) ..................... 12174020

(51) Int. Cl.
*C07K 14/49* (2006.01)
*C07K 14/47* (2006.01)
*C07K 14/71* (2006.01)

(52) U.S. Cl.
CPC .............. *C07K 14/47* (2013.01); *C07K 14/49* (2013.01); *C07K 14/71* (2013.01); *C07K 2318/20* (2013.01)

(58) Field of Classification Search
CPC ............... C07K 14/49; C07K 2318/20; A61K 38/1858; C12N 15/1044
See application file for complete search history.

(56) References Cited

U.S. PATENT DOCUMENTS

| | | | |
|---|---|---|---|
| 5,094,941 A * | 3/1992 | Hart ................. | 435/7.9 |
| 7,417,130 B2 * | 8/2008 | Stumpp et al. ........... | 536/23.1 |
| 8,110,653 B2 * | 2/2012 | Stumpp et al. ........... | 530/300 |
| 8,710,187 B2 * | 4/2014 | Binz et al. ............... | 530/350 |
| 8,722,618 B2 * | 5/2014 | Jacobs et al. ............ | 514/1.7 |
| 2004/0132028 A1 * | 7/2004 | Stumpp et al. .......... | 435/6 |
| 2009/0082274 A1 * | 3/2009 | Stumpp et al. .......... | 514/12 |
| 2009/0215197 A1 * | 8/2009 | Shiotsuka et al. ....... | 436/501 |
| 2010/0317599 A1 * | 12/2010 | Los et al. ................. | 514/21.2 |
| 2011/0207668 A1 * | 8/2011 | Binz et al. ............... | 514/13.3 |
| 2011/0262964 A1 * | 10/2011 | Bedouelle et al. ...... | 435/69.1 |
| 2012/0142611 A1 * | 6/2012 | Stumpp et al. .......... | 514/21.2 |
| 2012/0277143 A1 * | 11/2012 | Jacobs et al. ............ | 514/1.7 |
| 2012/0309940 A1 * | 12/2012 | Fischer et al. .......... | 530/387.3 |
| 2013/0116197 A1 * | 5/2013 | Binz et al. ............... | 514/20.8 |
| 2013/0244940 A1 * | 9/2013 | Steiner et al. ........... | 514/15.2 |
| 2013/0296221 A1 * | 11/2013 | Binz ........................ | 514/1.1 |

FOREIGN PATENT DOCUMENTS

| | | |
|---|---|---|
| WO | 02/20565 | 3/2002 |
| WO | 2006/129828 | 12/2006 |
| WO | 2009/068649 | 6/2009 |
| WO | 2011/135067 | 11/2011 |
| WO | WO 2012/069655 * | 5/2012 |

OTHER PUBLICATIONS

Binz et al. "High-affinity binders selected from designed ankyrin repeat protein libraries," Nature Biotechnology, May 2004, vol. 22, No. 5, pp. 575-582.*
Zweifel et al. "Structure and stability of the ankyrin domain of the Drosophila Notch receptor," Protein Science (2003), 12:2622-2632.*
Green et al. "Inhibitory DNA Ligands to Platelet-Derived Growth Factor B-Chain," Biochemistry 1996, 35, 14413-14424.*
Dreier et al. "Rapid Selection of High-Affinity Binders Using Ribosome Display," Chapter 15, Julie A. Douthwaite and Ronald H. Jackson (eds.), Ribosome Display and Related Technologies: Methods and Protocols, Methods in Molecular Biology, vol. 805, DOI 10.1007/978-1-61779-379-0_15.*
International Search Report for PCT/EP2013/063488, Sep. 19, 2013.*
Mosavi et al. "The ankyrin repeat as molecular architecture for protein recognition," Protein Science (2004), 13:1435-1448.*
Steiner et al. "Efficient Selection of DARPins with Sub-nanomolar Affinities using SRP Phage Display," J. Mol. Biol. (2008) 382, 1211-1227.*
Steiner et al. "Supplementary Material" to "Efficient Selection of DARPins with Sub-nanomolar Affinities using SRP Phage Display," J. Mol. Biol. (2008) 382, 1211-1227, pp. 1-17.*
Oefner et al. "Crystal structure of human platelet-derived growth factor BB," The EMBO Journal vol. 11 No. 11 pp. 3921-3926, 1992.*
Shim et al. "Structures of a platelet-derived growth factor/propeptide complex and a platelet-derived growth factor/receptor complex," PNAS, Jun. 22, 2010, vol. 107, No. 25, 11307-11312.*
Stumpp et al. "DARPins: A new generation of protein therapeutics," Drug Discovery Today_vol. 13, Nos. 15/16_Aug. 2008.*
European Search Report Issued Aug. 17, 2012 in corresponding European Application No. 12 17 4020.
H. Binz et al., "High-affinity binders selected from designed ankyrin repeat protein libraries", Nature Biotechnology, vol. 22, No. 5, May 2004, pp. 575-582.
M. Stumpp et al., "DARPins: A new generation of protein therapeutics", Drug Discovery Today, vol. 13, No. 15-16, Aug. 2008, pp. 695-701.
J. Shen et al., "An antibody directed against PDGF receptor β enhances the antitumor and the anti-angiogenic activities of an anti-VEGF receptor 2 antibody", Biochemical and Biophysical Research Communications, vol. 357, No. 4, May 2007, pp. 1142-1147.
H. Shan et al., "Inhibitory effect of soluble platelet-derived growth receptor β on intraosseous growth of breast cancer cells in nude mice", Cancer Science, vol. 102, No. 10, pp. 1904-1910, Oct. 2011.

* cited by examiner

*Primary Examiner* — Christina Bradley
(74) *Attorney, Agent, or Firm* — Wenderoth, Lind & Ponack, L.L.P.

(57) ABSTRACT

New designed ankyrin repeat proteins with binding specificity for PDGF-BB are described, as well as nucleic acids encoding such PDGF binding proteins, pharmaceutical compositions comprising such proteins and the use of such proteins in the treatment of diseases.

27 Claims, 3 Drawing Sheets

US 9,163,070 B2

DESIGNED ANKYRIN REPEAT PROTEINS BINDING TO PLATELET-DERIVED GROWTH FACTOR

FIELD OF THE INVENTION

The present invention relates to designed ankyrin repeat proteins with binding specificity for platelet-derived growth factor (PDGF), as well as nucleic acids encoding such PDGF binding proteins, pharmaceutical compositions comprising such proteins and the use of such proteins in the treatment of diseases.

BACKGROUND OF THE INVENTION

Platelet-derived growth factor (PDGF) was identified more than three decades ago as a serum growth factor for fibroblasts, smooth muscle cells and glia cells. Its role in physiology and medicine is extensively described in a recent review (Andrae, J., Gallini, R. and Betsholtz, C., Genes Dev., 22, 1276-1312, 2008). Human PDGF was originally identified as a disulfide-linked dimer of two different polypeptide chains, A (PDGF-A; human PDGF-A has the UniProtKB/Swiss-Prot number P04085) and B (PDGF-B; human PDGF-B has the UniProtKB/Swiss-Prot number P01127). Thereby, three protein dimers can be formed: PDGF-AA, PDGF-AB and PDGF-BB. Recently, two additional PDGF polypeptide chains, PDGF-C and PDGF-D, were identified. The currently known PDGF genes and polypeptides belong to a family of structurally and functionally related growth factors including also the vascular endothelial growth factors (VEGFs). PDGF/VEGF growth factors are conserved throughout the animal kingdom.

PDGFs act via two receptor tyrosine kinases (RTKs), PDGF receptor (PDGFR) alpha (PDGFRalpha) and beta (PDGFRbeta), with common domain structures, including five extracellular immunoglobulin (Ig) loops and a split intracellular tyrosine kinase domain. The VEGFs act through a distinct but structurally related subfamily of RTKs. Ligand binding promotes receptor dimerization, which initiates signaling. Depending on ligand configuration and the pattern of receptor expression, different receptor dimers may form. However, only a few interactions seem to be relevant in vivo; i.e., those of PDGF-AA and PDGF-CC via PDGFRalpha, and PDGF-BB via PDGFRbeta.

The PDGFs have crucial roles during development, but there is limited evidence for normal physiological functions in the adult. Studies of PDGFs and PDGFRs in animal development have revealed roles for PDGFRalpha signaling in gastrulation and in the development of the cranial and cardiac neural crest, gonads, lung, intestine, skin, CNS, and skeleton. Similarly, roles for PDGFRbeta signaling have been established in blood vessel formation and early hematopoiesis. PDGF signaling is implicated in a range of diseases. Autocrine activation of PDGF signaling pathways is involved in certain gliomas, sarcomas, and leukemias. Paracrine PDGF signaling is commonly observed in epithelial cancers, where it triggers stromal recruitment and may be involved in epithelial-mesenchymal transition, thereby affecting tumor growth, angiogenesis, invasion, and metastasis. PDGFs drive pathological mesenchymal responses in vascular disorders such as atherosclerosis, restenosis, pulmonary hypertension, and retinal diseases, as well as in fibrotic diseases, including pulmonary fibrosis, liver cirrhosis, scleroderma, glomerulosclerosis, and cardiac fibrosis.

Thus, increased PDGF activity has been linked with several diseases and pathological conditions. Causal pathogenic roles of the PDGFs have been established for some diseases, providing prospects for therapy using PDGF antagonists, such as PDGF specific antibodies. In addition, it has been suggested that the combination of anti-VEGF and anti-PDGF agents affords synergistic therapeutic benefits for treating certain ocular neovascular diseases (WO 2005/020972; Jo, N., Mailhos, C., Ju, M., Cheung, E., Bradley, J., Nishijima, K., Robinson, G. S., Adamis, A. P. and Shima, D. T., Am. J. Pathol., 168(6), 2036-2053, 2006).

There are, beside antibodies, novel binding proteins or binding domains that can be used to specifically bind a target molecule (e.g. Binz, H. K., Amstutz, P. and Plückthun, A., Nat. Biotechnol. 23, 1257-1268, 2005) and thereby act as an antagonist. One such novel class of binding proteins or binding domains not possessing an Fc are based on designed repeat proteins or designed repeat domains (WO 2002/020565; Binz, H. K., Amstutz, P., Kohl, A., Stumpp, M. T., Briand, C., Forrer, P., Grütter, M. G., and Plückthun, A., Nat. Biotechnol. 22, 575-582, 2004; Stumpp, M. T., Binz, H. K and Amstutz, P., Drug Discov. Today 13, 695-701, 2008). WO 2002/020565 describes how large libraries of repeat proteins can be constructed and their general application. Nevertheless, WO 2002/020565 does neither disclose the selection of repeat domains with binding specificity for PDGF-BB nor concrete repeat modules or repeat sequence motifs of repeat domains that specifically bind to PDGF-BB. Furthermore, WO 2002/020565 does not suggest that repeat domains with binding specificity for PDGF-BB could be used to regulate the PDGF-BB mediated signaling pathways to successfully treat diseases. These designed repeat domains harness the modular nature of repeat proteins and may possess N-terminal and C-terminal capping modules to prevent the designed repeat domains from aggregation by shielding the hydrophobic core of the domain (Forrer, P., Stumpp, M. T., Binz, H. K. and Plückthun, A., FEBS letters 539, 2-6, 2003).

The technical problem underlying the present invention is identifying novel binding proteins, such as ankyrin repeat proteins or domains, with binding specificity to PDGF-BB to regulate PDGF-BB mediated signaling pathways for an improved treatment of certain cancers, vascular disorders such as retinal diseases, fibrotic diseases and other pathological conditions. The solution to this technical problem is achieved by providing the embodiments characterized in the claims.

SUMMARY OF THE INVENTION

The present invention relates to a recombinant binding protein comprising at least one ankyrin repeat domain, wherein said ankyrin repeat domain binds PDGF-BB in PBS with a Kd below $10^{-7}$M.

More particularly, the invention relates to a recombinant binding protein comprising at least one ankyrin repeat domain, wherein said ankyrin repeat domain competes for binding to PDGF-BB with an ankyrin repeat domain selected from the group consisting of SEQ ID NOs: 23 to 60, or wherein said ankyrin repeat domain is selected from the group consisting of SEQ ID NOs:23 to 60 wherein G at position 1 and/or S at position 2 of said ankyrin repeat domain are optionally missing; and L at the second last position and/or N at the last position of said ankyrin repeat domain are optionally exchanged by A.

In a further embodiment, the invention relates to a recombinant PDGF-BB binding protein comprising at least one ankyrin repeat domain, which comprises an ankyrin repeat module having an amino acid sequence selected from the group consisting of SEQ ID NO: 12, 14, 15, 17, 18 and 19 and sequences, wherein up to 9 amino acids in SEQ ID NO: 12, 14, 15, 17, 18 and 19 are exchanged by any amino acid.

In particular the invention relates to a recombinant PDGF-BB binding protein comprising a peptide of any one of the sequences SEQ ID NO: 12 to 19 and 23 to 61.

The invention further relates to nucleic acid molecules encoding the binding proteins of the present invention, and to a pharmaceutical composition comprising one or more of the above mentioned binding proteins or nucleic acid molecules.

The invention further relates to a method of treatment of a pathological condition using the binding proteins of the invention.

OD, optical density at 450 nm; C, concentration of DARPin #49 in nM; D1, DARPin #49. The X axis is shown in logarithmic scale. See below for the definition of DARPin #49.

Figure 2:
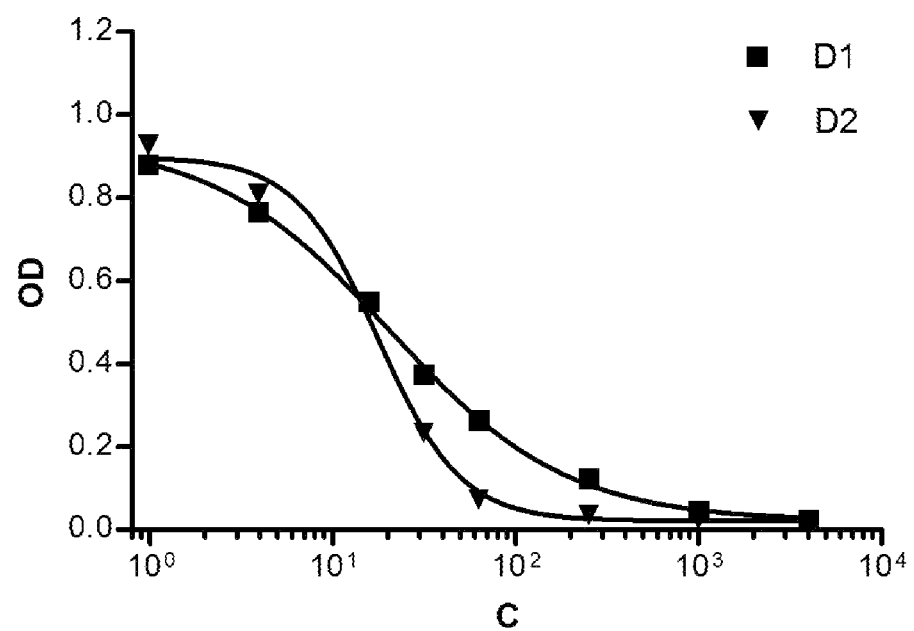

FIG. 2. PDGFRbeta competition assay.
The inhibition of the binding of PDGF-BB to PDGFRbeta by various concentrations of DARPins with specificity for PDGF-BB and the corresponding fitted inhibition curves are shown for a distinct single experiment. The $IC_{50}$ values were then calculated to be about 20 and 18 pM for the DARPins #50 (D1) and #28 (D2), respectively. OD, optical density at 450 nm; C, concentration of DARPins in pM. The X axis is shown in logarithmic scale. See below for the definitions of DARPin #50 and 28.

Figure 3:
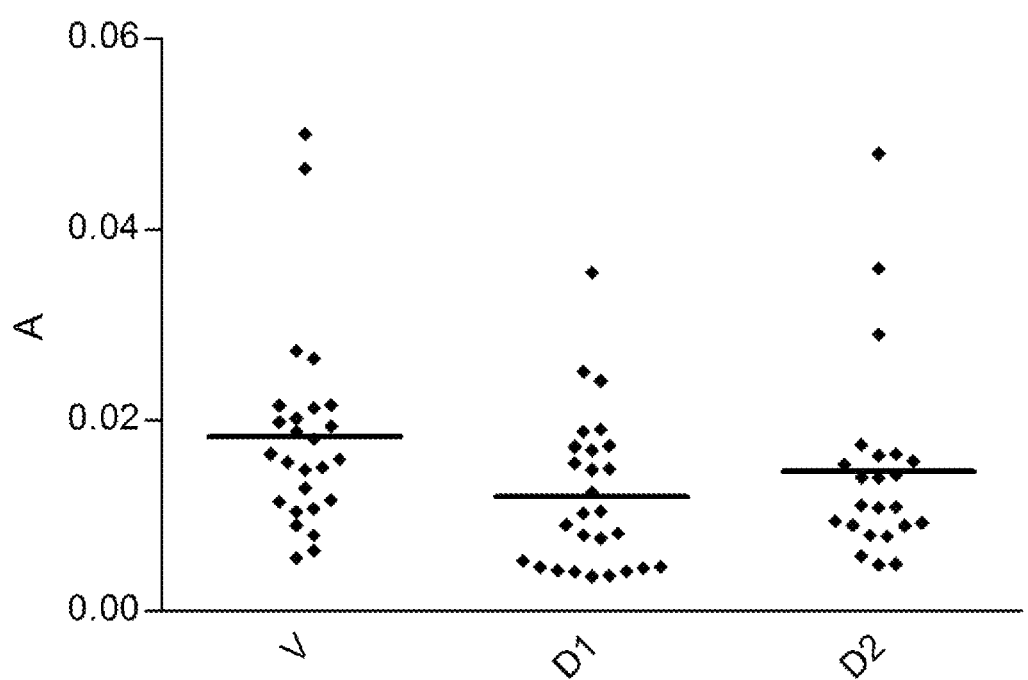

FIG. 3. Effects of an anti-PDGF-BB DARPin vs vehicle on the development of choroidal neovascularization.
Mice were daily injected intraperitoneal with vehicle or DARPin #61-PEG20 (i.e. DARPin #61 conjugated to PEG20 over its C-terminal Cys residues by standards means (e.g. as described in WO 2011/135067)) from day 0 until day 14. At day 2 the laser burns were applied to the eye to induce choroidal neovascularization (CNV) and at day 14 the extent of CNV was measured. Symbols represent individual eyes and represent mean values of three induced CNV spots each. Bars represent median values of the individual groups. A, Area of CNV in $mm^2$; V, vehicle (i.e. PBS); D1, DARPin #61-PEG20 in PBS at a 10 mg/kg per dose injected; D2, DARPin #61-PEG20 in PBS at a 1 mg/kg per dose injected.

DETAILED DESCRIPTION OF THE INVENTION

The recombinant binding protein or domain according to the invention is specific for a mammalian PDGF-BB. Preferably, the recombinant binding domain according to the invention is specific for a PDGF-BB of mice, rat, dog, rabbit, monkey or human origin. More preferably, the recombinant binding domain according to the invention is specific for a PDGF-BB of human origin.

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structures, is termed "protein domain". Such protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen), yeast expression plasmid or mammalian expression plasmid. When, for example, such a constructed recombinant bacterial expression plasmid is inserted into an appropriate bacteria (e.g. *Escherichia coli*), this bacteria can produce the polypeptide encoded by this recombinant DNA. The correspondingly produced polypeptide is called a recombinant polypeptide.

In the context of the present invention, the term "polypeptide" relates to a molecule consisting of one or more chains of multiple, i.e. two or more, amino acids linked via peptide bonds. Preferably, a polypeptide consists of more than eight amino acids linked via peptide bonds.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag of SEQ ID NO:9), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 2002/020565. Particular examples of such linkers are glycine-serine-linkers and proline-threonine-linkers of variable lengths; preferably, said linkers have a length between 2 and 24 amino acids; more preferably, said linkers have a length between 2 and 16 amino acids. An example of a glycine-serine-linker is provided in SEQ ID NO:10 and an example of a proline-threonine-linker is provided in SEQ ID NO:11. Preferably, the proline-threonine-linker of SEQ ID NO:11 is preceded by GS and/or followed by GS.

The term "polymer moiety" refers to either a proteinaceous polymer moiety or a non-proteinaceous polymer moiety. A "proteinaceous polymer moiety" preferably is a polypeptide that does not form a stable tertiary structure. Examples of proteinaceous polymer moieties are XTEN® (a registered trademark of Amunix; WO 2007/103515) polypeptides, or polypeptides comprising proline, alanine and serine residues as described in WO 2008/155134. Such proteinaceous polymer moieties can be covalently attached to, for example, a binding domain of the invention by the generation of genetic fusion polypeptides using standard DNA cloning technologies, followed by their standard expression and purification. A "non-proteinaceous polymer moiety" is a polymer moiety not built from polypeptides. Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention. A polymer moiety of the invention may vary widely in molecular weight. Preferably, said polymer moiety is connected by a polypeptide linker to a binding domain.

In a specific embodiment, a PEG moiety or any other non-proteinaceous polymer can, e.g., be coupled to a cysteine thiol via a maleimide linker with the cysteine being coupled via a peptide linker to the N- or C-terminus of a binding domain as described herein.

The term "binding protein" refers to a protein comprising one or more binding domains, one or more bioactive compounds and one or more polymer moieties as further explained below. Preferably, said binding protein comprises up to four binding domains. More preferably, said binding protein comprises up to two binding domains. Most preferably, said binding protein comprises only one binding domain. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art. Preferably, said binding protein is a recombinant binding protein. Also preferably, the binding domains of binding protein possess different target specificities.

The term "bioactive compound" refers to a compound that is disease modifying when applied to a mammal having said disease. A bioactive compound may have antagonistic or agonistic properties and can be a proteinaceous bioactive compound or a non-proteinaceous bioactive compound. Such proteinaceous bioactive compounds can be covalently attached to, for example, a binding domain of the invention by the generation of genetic fusion polypeptides using standard DNA cloning technologies, followed by their standard expression and purification. Such non-proteinaceous bioactive compounds can be covalently attached to, for example, a binding domain of the invention by chemical means, e.g., by coupling to a cysteine thiol via a maleimide linker with a cysteine being coupled via a peptide linker to the N- or C-terminus of a binding domain as described herein. Examples of proteinaceous bioactive compounds are binding domains having a distinct target specificity (e.g. neutralizing a growth factor by binding to it), cytokines (e.g. interleukins), growth factors (e.g. human growth hormone), antibodies and fragments thereof, hormones (e.g. GLP-1) and any possible proteinaceous drug. Examples of non-proteinaceous bioactive compounds are, toxins (e.g. DM1 from ImmunoGen), small molecules targeting GPCRs, antibiotics and any possible non-proteinaceous drug.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Binz et al., 2005, loc. cit.). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display. Preferably, said binding domain is a recombinant binding domain.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In the particular application of the present invention, the target is PDGF-BB.

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

The definitions hereinafter for repeat proteins are based on those in patent application WO 2002/020565. Patent application WO 2002/020565 further contains a general description of repeat protein features, techniques and applications.

The term "repeat proteins" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create a superhelical structure having a joint hydrophobic core. Preferably, a repeat domain further comprises an N-terminal and/or a C-terminal capping unit (or module). Even more preferably, said N-terminal and/or C-terminal capping units (or modules) are capping repeats.

The term "designed repeat protein" and "designed repeat domain" refer to a repeat protein or repeat domain, respectively, obtained as the result of the inventive procedure explained in patent application WO 2002/020565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system. Accordingly, a designed ankyrin repeat protein (i.e. a DARPin) corresponds to a recombinant binding protein of the invention comprising at least one ankyrin repeat domain.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units correspond to the "repeating structural units (repeats)" of repeat proteins as described by Forrer et al., 2003, loc. cit. or the "consecutive homologous structural units (repeats)" of repeat proteins as described by Binz et al, 2004, loc. cit. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

Accordingly, the term "ankyrin repeat unit" shall mean a repeat unit, which is an ankyrin repeat as described, for example, by Forrer et al., 2003, loc. cit. Ankyrin repeats are well known to the person skilled in the art. The term "ankyrin repeat domain" refers to a repeat domain comprising two or more consecutive ankyrin repeat units (modules) as structural units, and, preferably, an N-terminal and/or a C-terminal capping unit (or module).

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (or module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous to each other. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art. Further preferably, the repeat units used for the deduction of a repeat sequence motif are homologous repeat units obtained from repeat domains selected on a defined target.

The term "repeat sequence motif" refers to an amino acid sequence, which is deduced from one or more repeat units or repeat modules. Preferably, said repeat units or repeat modules are from repeat domains having binding specificity for the same target. Such repeat sequence motifs comprise framework residue positions and target interaction residue positions. Said framework residue positions correspond to the positions of framework residues of the repeat units (or modules). Likewise, said target interaction residue positions correspond to the positions of target interaction residues of the repeat units (or modules). Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues and/or the positions of target interaction residues that are specific for a certain target. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. Most often, such randomized positions correspond to the positions of target interaction residues. However, some positions of framework residues may also be randomized.

The term "folding topology" refers to the tertiary structure of said repeat units or repeat modules. The folding topology will be determined by stretches of amino acids forming at least parts of α-helices or β-sheets, or amino acid stretches forming linear polypeptides or loops, or any combination of α-helices, β-sheets and/or linear polypeptides/loops. For example, an ankyrin repeat unit/module consists of a β-turn, followed by two antiparallel α-helices and a loop that reaches the turn of the next repeat unit/module.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units (or modules). In most cases, repeat units (or modules) of a repeat domain will exhibit a high degree of sequence identity (same amino acid residues at corresponding positions) or sequence similarity (amino acid residues being different, but having similar physicochemical properties), and some of the amino acid residues might be key residues being strongly conserved. However, a high degree of sequence variability by amino acid insertions and/or deletions, and/or substitutions between the different repeat units (or modules) of a repeat domain may be possible as long as the common folding topology of the repeat units (or modules) is maintained.

Methods for directly determining the folding topology of repeat proteins by physicochemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins. Further preferably, each repeat module comprised in a repeat domain comprises a repeat sequence motif deduced from homologous repeat units obtained from repeat domains selected on a target, for example as described in Example 1 and having the same target specificity.

Accordingly, the term "ankyrin repeat module" shall mean a repeat module, which is originally derived from the repeat units of naturally occurring ankyrin repeat proteins. Ankyrin repeat proteins are well known to the person skilled in the art.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein said capping module forms tight tertiary interactions (i.e. tertiary structure interactions) with said repeat module thereby providing a cap that shields the hydrophobic core of said repeat module at the side not in contact with the consecutive repeat module from the solvent. Said N- and/or C-terminal capping module may be, or may be derived from, a capping unit or other structural unit found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary structure interactions with said repeat unit thereby providing a cap that shields the hydrophobic core of said repeat unit at one side from the solvent. Preferably, capping modules or capping units are capping repeats. The term "capping repeat" refers to capping module or capping unit having a similar or the same fold as said adjacent repeat unit (or module) and/or sequence similarities to said adjacent repeat unit (or module). Capping modules and capping repeats are described in WO 2002/020565 and by Interlandi et al., 2008 (loc. cit.). Examples of N-terminal ankyrin capping modules (i.e. N-terminal capping repeats) are SEQ ID NO:1 to 3 and examples of ankyrin C-terminal capping modules (i.e. C-terminal capping repeats) are SEQ ID NO:4 to 8, 13 and 16.

For example, the N-terminal ankyrin capping module of SEQ ID NO:49 is encoded by the amino acids from position 1 to 32 and the C-terminal capping module of SEQ ID NO:49 is encoded by the amino acids form position 132 to 159.

A recombinant binding protein according to the invention comprises at least one ankyrin repeat domain, wherein said ankyrin repeat domain has binding specificity for mammalian PDGF-BB.

The term "has binding specificity for a target", "specifically binding to a target" or "target specificity" and the like means that a binding protein or binding domain binds in PBS to a target with a lower dissociation constant than to an unrelated protein such as the $E.\ coli$ maltose binding protein (MBP). Preferably, the dissociation constant in PBS for the target is at least 10, more preferably at least $10^2$, even more preferably at least $10^3$, or most preferably at least $10^4$ times lower than the corresponding dissociation constant for MBP.

Recombinant binding proteins comprising an ankyrin repeat domain with binding specificity for PDGF-BB are shown in the Examples.

In particular, the invention relates to a recombinant binding protein as defined herein comprising an ankyrin repeat domain with binding specificity for PDGF-BB, which binds PDGF-BB in PBS with a dissociation constant (Kd) below $10^{-6}$M. Preferably, said ankyrin repeat domain binds PDGF-BB with a Kd in PBS below $10^{-7}$M, more preferably below $10^{-8}$M, $10^{-6}$M, $10^{-10}$M, or most preferably below $10^{-11}$M.

Methods to determine dissociation constants of protein-protein interactions, such as surface plasmon resonance (SPR) based technologies (e.g. SPR equilibrium analysis) or isothermal titration calorimetry (ITC) are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

Recombinant binding proteins comprising an ankyrin repeat domain binding PDGF-BB with a Kd in PBS below $10^{-6}$M are shown in Example 2.

Preferred is a recombinant binding protein comprising an ankyrin repeat domain with binding specificity for human PDGF-BB.

Further preferred is a recombinant binding protein comprising an ankyrin repeat domain comprising between 70 and 300 amino acids, in particular between 90 and 200 amino acids.

A binding domain of the invention is an ankyrin repeat domain or a designed ankyrin repeat domain, preferably as described in WO 2002/020565. Examples of designed ankyrin repeat domains with binding specificity for PDGF-BB are shown in the Examples.

In a further embodiment, the invention relates to a recombinant binding protein comprising at least one ankyrin repeat domain with binding specificity for a mammalian PDGF-BB, wherein the ankyrin repeat domain inhibits the binding of PDGF-BB to PDGFRbeta in PBS with an $IC_{50}$ value below $10^{-7}$M. Preferably, said ankyrin repeat domain inhibits the binding of PDGF-BB to PDGFRbeta in PBS with an $IC_{50}$ value below $10^{-7}$M, more preferably below $10^{-8}$M, $10^{-9}$M, $10^{-10}$M, or most preferably below $10^{-11}$M.

The half maximal inhibitory concentration ($IC_{50}$) is a measure of the effectiveness of a compound, such as a binding domain of the invention, in inhibiting a biological, biochemical or biophysical function. Methods to determine $IC_{50}$ values of inhibition of protein-protein interactions, such as competition ELISAs are well known to the person skilled in the art. The measured $IC_{50}$ values of a particular inhibitor of a protein-protein interaction can vary if measured under different conditions (e.g., salt concentration, pH). Thus, measurements of $IC_{50}$ values are preferably made with standardized solutions of protein and a standardized buffer, such as PBS.

Recombinant binding proteins comprising an ankyrin repeat domain inhibiting the binding of PDGF-BB to PDGFRbeta in PBS with an $IC_{50}$ value below $10^{-7}$M are shown in Example 4.

In a further embodiment, the invention relates to a recombinant binding protein comprising at least one ankyrin repeat domain with binding specificity for PDGF-BB, which inhibits the PDGF-BB stimulated proliferation of NIH-3T3 fibroblasts (ATCC, cat number: CRL-1658) with an $IC_{50}$ value below $10^{-6}$M. Preferably, said repeat domain inhibits the PDGF-BB stimulated proliferation of NIH-3T3 fibroblasts with an $IC_{50}$ value below $10^{-7}$M, more preferably below $10^{-8}$M, $10^{-9}$M, $10^{-10}$M, or most preferably $10^{-11}$M.

NIH-3T3 cells are responsive to PDGF-BB for growth and as such can be used to measure the functional inhibitory capability of the compounds of the invention. NIH-3T3 cells are grown in culture medium and then starved of nutrients for 7 hours prior to addition of PDGF-BB and a titration of the anti-PDGF-BB DARPin. Assessment of the ability of the compounds of the invention to inhibit PDGF-BB is determined by the proliferative capacity of the NIH-3T3 cells as measured by standard measurements well known to the person skilled in the art. Recombinant binding proteins comprising an ankyrin repeat domain inhibiting the PDGF-BB stimulated proliferation of NIH-3T3 fibroblasts with an $IC_{50}$ value below $10^{-6}$M are shown in Example 3.

The invention relates to a recombinant binding protein comprising at least one ankyrin repeat domain with binding specificity for PDGF-BB, wherein said binding protein and/or ankyrin repeat domain has a midpoint denaturation temperature (Tm) above 40° C. upon thermal unfolding in PBS and forms less than 5% (w/w) insoluble aggregates at concentrations up to 10 g/L when incubated at 37° C. for 1 day in PBS.

The term "PBS" means a phosphate buffered water solution containing 137 mM NaCl, 10 mM phosphate and 2.7 mM KCl and having a pH of 7.4.

Preferably, the recombinant binding protein and/or binding domain has a midpoint denaturation temperature (Tm) above 45° C., more preferably above 50° C., more preferably above 55° C., and most preferably above 60° C. upon thermal unfolding in PBS at pH 7.4. A binding protein or a binding domain of the invention possesses a defined secondary and tertiary structure under physiological conditions. Thermal unfolding of such a polypeptide results in a loss of its tertiary and secondary structure, which can be followed, for example, by circular dichroism (CD) measurements. The midpoint denaturation temperature of a binding protein or binding domain upon thermal unfolding corresponds to the temperature at the midpoint of the cooperative transition in physiological buffer upon heat denaturation of said protein or domain by slowly increasing the temperature from 10° C. to about 100° C. The determination of a midpoint denaturation temperature upon thermal unfolding is well known to the person skilled in the art. This midpoint denaturation temperature of a binding protein or binding domain upon thermal unfolding is indicative of the thermal stability of said polypeptide.

Also preferred is a recombinant binding protein and/or ankyrin repeat domain forming less than 5% (w/w) insoluble aggregates at concentrations up to 20 g/L, preferably up 40 g/L, more preferably up to 60 g/L, even more preferably up to 80 g/L, and most preferably up to 100 g/L when incubated for over 5 days, preferably over 10 days, more preferably over 20 days, more preferably over 40 days, and most preferably over 100 days at 37° C. in PBS. The formation of insoluble aggregates can be detected by the appearance of visual precipitations, gel filtration or dynamic light scattering, which strongly increases upon formation of insoluble aggregates. Insoluble aggregates can be removed from a protein sample by centrifugation at 10,000×g for 10 minutes. Preferably, a recombinant binding protein and/or ankyrin repeat domain forms less than 2%, more preferably less than 1%, 0.5%, 0.2%, 0.1%, or most preferably less than 0.05% (w/w) insoluble aggregates under the mentioned incubation conditions at 37° C. in PBS. Percentages of insoluble aggregates can be determined by separation of the insoluble aggregates from soluble protein, followed by determination of the protein amounts in the soluble and insoluble fraction by standard quantification methods.

Also preferred is a recombinant binding protein and/or ankyrin repeat domain that does not lose its native three-dimensional structure upon incubation in PBS containing 100 mM dithiothreitol (DTT) for 1 or 10 hours at 37° C.

In one particular embodiment the invention relates to a recombinant binding protein comprising an ankyrin repeat domain, specifically binding to PDGF-BB and having the indicated or preferred midpoint denaturation temperature and non-aggregating properties as defined above.

In a further embodiment, the invention relates to a recombinant binding protein comprising at least one ankyrin repeat domain with binding specificity for a mammalian PDGF-BB, wherein the ankyrin repeat domain competes for binding to a mammalian PDGF-BB with an ankyrin repeat domain selected from the group consisting of SEQ ID NOs: 23 to 60; preferably SEQ ID NOs: 24, 45 and 50, in particular SEQ ID NO:24 and 50.

Also preferably said ankyrin repeat domain competes for binding to a mammalian PDGF-BB with a binding protein selected from the group of DARPins #23 to 60. Preferably, said repeat domain competes for binding to a mammalian PDGF-BB with a binding protein from the group of DARPins #24, 45 and 50. More preferably, said ankyrin repeat domain competes for binding to a mammalian PDGF-BB with binding protein DARPin #24 or 50.

The term "compete for binding" means the inability of two different binding domains of the invention to bind simultaneously to the same target, while both are able to bind the same target individually. Thus, such two binding domains compete for binding to said target. Preferably, said two competing binding domains bind to an overlapping or the same binding epitope on said target. Methods, such as competition Enzyme-Linked Immuno Sorbent Assay (ELISA) or competition SPR measurements (e.g. by using the Proteon instrument from BioRad), to determine if two binding domains compete for binding to a target, are well known to the practitioner in the art. For example, the ankyrin repeat domain of SEQ ID No: #49 or SEQ ID No: #58 competes for binding to human PDGF with the ankyrin repeat domain of SEQ ID No: #50.

The term "epitope" means the specific site on the surface of a target protein, such as PDGF-BB, to which a binding domain of the invention, such as an ankyrin repeat domain, attaches itself. This term is defined in analogy to epitopes of antibodies, which are well known to the person skilled in the art. If two binding domains of the invention bind to the same epitope, they will compete for binding for PDGF-BB. The exact molecular arrangement of an epitope can be elucidated, for example, by protein X-ray crystallography (a method well known to the person skilled in the art) of the binding domain of the invention in complex with PDGF-BB.

In a further embodiment, the invention relates to a recombinant binding protein comprising at least one ankyrin repeat domain with binding specificity for a mammalian PDGF-BB, wherein said ankyrin repeat domain comprises an amino acid sequence that has at least 70% amino acid sequence identity with one ankyrin repeat domain selected from the group consisting of SEQ ID NOs: 23 to 60,
wherein G at position 1 and/or S at position 2 of said ankyrin repeat domain are optionally missing; and
L at the second last position and/or N at the last position of said ankyrin repeat domain are optionally exchanged by A.

Preferably, such an ankyrin repeat domain in a recombinant binding protein of the invention comprises an amino acid sequence that has at least 70% amino acid sequence identity with one ankyrin repeat domain selected from the group consisting of SEQ ID NO: 24, 45 and 50; more preferably, 24 and 50.

Preferably, such an ankyrin repeat domain in a recombinant binding protein of the invention comprises an amino acid sequence with at least 70% amino acid sequence identity, for example 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% amino acid sequence identity with one, two or three ankyrin repeat modules present between the N-terminal and C-terminal capping modules of an ankyrin repeat domain selected from the group consisting of SEQ ID NOs: 23 to 60.

Preferably, instead of 70% amino acid sequence identity, such an ankyrin repeat domain or such one, two or three repeat modules present between the N-terminal and C-terminal capping modules in an ankyrin repeat domain in a recombinant binding protein of the invention comprises an amino acid sequence with at least 75%, more preferably at least 76%, more preferably at least 80%, more preferably at least 85%, more preferably at least 90%, or most preferred at least 95% amino acid sequence identity. Preferably, the mentioned percentages of amino acid sequence identity is in the framework positions.

Preferably, up to 30 amino acids, for example 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or no amino acid(s) in the repeat domains SEQ ID NO:23 to 60 are exchanged by another amino acid. In particular, up to 25 amino acids, more preferably up to 20 amino acids, more preferably up to 15 amino acids, even more preferably up to 11 amino acids, more preferably up to 8 amino acids, more preferably up to 5 amino acids, more preferably up to 2 amino acid, and most preferably no amino acid in SEQ ID NO: 23 to 60 is exchanged.

Preferably, when amino acids are exchanged in the capping modules of SEQ ID NO:13 or 16, the repeat modules of SEQ ID NO:12, 14, 15, 17, 18 and 19 or the repeat domains of SEQ ID NO:23 to 60, these amino acids are selected from the group consisting of A, D, E, F, H, I, K, L, M, N, Q, R, S, T, V, W and Y; more preferably from the group consisting of A, D, E, H, I, K, L, Q, R, S, T, V, and Y. Also preferably, an amino acid is exchanged by a homologous amino acid; i.e. an amino acid is exchanged by an amino acid having a side chain with similar biophysical properties. For example, the negative charged amino acid D may be replaced by the negative charged amino acid E, or a hydrophobic amino acid such as L may be replaced by A, I or V. The techniques of exchanging an amino acid by another amino acid in a polypeptide are well known to the person skilled in the art.

In a further embodiment, the invention relates to a recombinant binding protein comprising at least one ankyrin repeat domain with binding specificity for a mammalian PDGF-BB, wherein said ankyrin repeat domain is selected from the group consisting of SEQ ID NOs: 23 to 60,
wherein G at position 1 and/or S at position 2 of said ankyrin repeat domain are optionally missing; and
L at the second last position and/or N at the last position of said ankyrin repeat domain are optionally exchanged by A.

Preferably, such an ankyrin repeat domain is selected from the group consisting of SEQ ID NO: 24, 45 and 50; more preferably, 24 and 50.

In a further embodiment, the invention relates to a recombinant binding protein, wherein the ankyrin repeat domain attaches to the same epitope as an ankyrin repeat domain selected from the group consisting of SEQ ID NOs:23 to 60. Preferably, such an ankyrin repeat domain is selected from the group consisting of SEQ ID NO: 24, 45 and 50; more preferably, 24 and 50.

In a further embodiment, the invention relates to a recombinant binding protein comprising at least one ankyrin repeat domain with binding specificity for a mammalian PDGF-BB, wherein said ankyrin repeat domain comprises an ankyrin repeat module having an amino acid sequence selected from the group consisting of SEQ ID NO:12, 14, 15, 17, 18 and 19 and sequences, wherein up to 9 amino acids in SEQ ID NO:12, 14, 15, 17, 18 and 19 are exchanged by any amino acid.

Preferably, such an ankyrin repeat module of said ankyrin repeat domain is selected from the group consisting of SEQ ID NO: 12, 14 and 17; more preferably, 12 and 17.

Preferably, up to 8 amino acids in the repeat modules of SEQ ID NO:12, 14, 15, 17, 18 and 19 are exchanged by another amino acid, more preferably up to 7 amino acids, more preferably up to 6 amino acids, more preferably up to 5 amino acids, even more preferably up to 4 amino acids, more preferably up to 3 amino acids, more preferably up to 2 amino acids, and most preferably 1 amino acid. Preferably, the mentioned exchanges of amino acid are in the framework positions. Accordingly, up to 8 amino acids in framework positions of SEQ ID NO:12, 14, 15, 17, 18 and 19 are exchanged by any amino acid, preferably up to 7, 6, 5, 4, 3 or 2 amino acids, and most preferably 1 amino acid.

In a further embodiment, the invention relates to a recombinant binding protein, wherein the ankyrin repeat domain with binding specificity to PDGF-BB comprises a repeat module with the ankyrin repeat sequence KDEEGTTPLHYAAVWGHLEIVEVLLKAGADVNA (SEQ ID NO:12) and sequences, wherein up to 9 amino acids in SEQ ID NO:11 are exchanged by any amino acid and wherein
E at position 3 is optionally exchanged by an amino acid selected from the group consisting of D, W, Q, I and Y, preferably of D and W;
E at position 4 is optionally exchanged by an amino acid selected from the group consisting of T, D, Y, and S, preferably of T and D;
T at position 6 is optionally exchanged by an amino acid selected from the group consisting of S and F, preferably by S;
Y at position 11 is optionally exchanged by F;
V at position 14 is optionally exchanged by an amino acid selected from the group consisting of A, Y and T, preferably by A; and
W at position 15 is optionally exchanged by an amino acid selected from the group consisting of F, K, V, and Y, preferably of F and Y.

In a further embodiment, the invention relates to a recombinant binding protein comprising at least one ankyrin repeat domain with binding specificity for a mammalian PDGF-BB, wherein said ankyrin repeat domain comprises a capping module having an amino acid sequence selected from the group consisting of SEQ ID NO:13 and 16 and sequences, wherein up to 9 amino acids in SEQ ID NO:13 and 16 are exchanged by any amino acid.

Preferably, up to 8 amino acids in the capping modules of SEQ ID NO:13 and 16 comprised in said ankyrin repeat domain are exchanged by an other amino acid, more preferably up to 7 amino acids, more preferably up to 6 amino acids, more preferably up to 5 amino acids, even more preferably up to 4 amino acids, more preferably up to 3 amino acids, more preferably up to 2 amino acids, more preferably up to 1 amino acid, and most preferably no amino acid in SEQ ID NO:13 and 16 is exchanged.

In yet another embodiment, the invention relates to a recombinant binding protein,
wherein the ankyrin repeat domain with binding specificity to PDGF-BB comprises a C-terminal capping module with the sequence QDIYGATPADLAALVGHEDIAEVLQKLN (SEQ ID NO:13) and sequences, wherein up to 9 amino acids in SEQ ID NO:13 are exchanged by any amino acid wherein
I at position 3 is optionally exchanged by an amino acid selected from the group consisting of K, L, A and V, preferably L, A and V;
Y at position 4 is optionally exchanged by an amino acid selected from the group consisting of W. F and S, preferably, of W and F;
A at position 6 is optionally exchanged by K;
L at position 14 is optionally exchanged by an amino acid selected from the group consisting of F, Y and D, preferably of F and Y;
V at position 15 is optionally exchanged by an amino acid selected from the group consisting of L, I, A and N, preferably, L and I; and
V at position 23 is exchanged by an amino acid selected from the group consisting of I and L.

Preferred is a recombinant binding protein, wherein the ankyrin repeat domain comprises the ankyrin repeat module of SEQ ID NO:12 and the C-terminal capping module SEQ ID NO:13. Preferably, said C-terminal capping module directly follows said ankyrin repeat module in said ankyrin repeat domain.

In yet another embodiment, the invention relates to a recombinant binding protein, wherein the ankyrin repeat domain with binding specificity to PDGF-BB comprises a repeat module with the ankyrin repeat sequence KDQEGTTPLHFAASVGHLEIVEVLLKAGADVNA (SEQ ID NO:15) and sequences, wherein up to 9 amino acids in SEQ ID NO:15 are exchanged by any amino acid and wherein
Q at position 3 is optionally exchanged by A;
E at position 4 is optionally exchanged by D;
T at position 6 is optionally exchanged by E;
F at position 11 is optionally exchanged by Y;
S at position 14 is optionally exchanged by V; and
V at position 15 is optionally exchanged by W.

In yet another embodiment, the invention relates to a recombinant binding protein,
wherein the ankyrin repeat domain with binding specificity to PDGF-BB comprises a C-terminal capping module with the sequence QDHYGATPADLAALIGHEDIAEVLQKLN (SEQ ID NO:16) and sequences, wherein up to 9 amino acids in SEQ ID NO:15 are exchanged by any amino acid and wherein
H at position 3 is optionally exchanged by I; and
Y at position 4 is optionally exchanged by W.

In yet another embodiment, the invention relates to a recombinant binding protein,
wherein the ankyrin repeat domain with binding specificity to PDGF-BB comprises a repeat module with the ankyrin repeat sequence KDLNGQTPLHLAADIGHLEIVEVLLKAGADVNA (SEQ ID NO:17) and sequences, wherein up to 9 amino acids in SEQ ID NO:17 are exchanged by any amino acid and wherein
K at position 1 is optionally exchanged by Q or I;
L at position 3 is optionally exchanged by N; and
A at position 27 is optionally exchanged by H.

In yet another embodiment, the invention relates to a recombinant binding protein,
wherein the ankyrin repeat domain with binding specificity to PDGF-BB comprises a repeat module with the ankyrin repeat sequence KDYAGSTPLRLAAWAGHLEIVEVLLKAGADVNA (SEQ ID NO:18) and sequences, wherein up to 9 amino acids in SEQ ID NO:18 are exchanged by any amino acid and wherein
K at position 1 is optionally exchanged by Q;
W at position 14 is optionally exchanged by H;
A at position 15 is optionally exchanged by V; and
A at position 27 is optionally exchanged by N or Y.

In yet another embodiment, the invention relates to a recombinant binding protein, wherein the ankyrin repeat domain with binding specificity to PDGF-BB comprises a repeat module with the ankyrin repeat sequence KDYFGYTPLHLAAYFGHLEIVEVLLKAGADVNA (SEQ ID NO:19) and sequences, wherein up to 9 amino acids in SEQ ID NO:19 are exchanged by any amino acid and wherein
K at position 1 is optionally exchanged by N;
A at position 12 is optionally exchanged by T;
A at position 13 is optionally exchanged by T;
E at position 22 is optionally exchanged by D;
A at position 27 is optionally exchanged by H or Y.

Further preferred is a N-terminal or C-terminal ankyrin capping module comprising an N-terminal or C-terminal ankyrin capping repeat, respectively, wherein one or more of the amino acids residues in said capping repeat are replaced by an amino acid residue found at the corresponding position on alignment of a corresponding ankyrin capping unit or ankyrin repeat unit.

The replacement of amino acids can be by any of the 20 most often naturally occurring amino acids, preferably by amino acids selected from the group consisting of A, D, E, F, H, I, K, L, M, N, Q, R, S, T, V, W and Y; and more preferably from the group consisting of A, D, E, H, I, K, L, Q, R, S, T, V, and Y. Also preferably, the replacement of amino acids is by a homologous amino acid; i.e. an amino acid is replaced by an amino acid having a side chain with similar biophysical properties. For example, the negative charged amino acid D may be replaced by the negative charged amino acid E, or a hydrophobic amino acid such as L may be replaced by A, I or V. The replacement of an amino acid by a homologous amino acid is well known to the person skilled in the art.

Also preferred is a C-terminal ankyrin capping module comprising the amino acid A at position 27 and 28 of any of the above C-terminal capping modules based on SEQ ID NO:4 to 8, 13 and 16.

Also preferred is a C-terminal capping module comprising the amino acids from position 1 to 26 or from position 1 to 27 of any of the above C-terminal capping modules based on SEQ ID NO:4 to 8, 13 and 16.

Amino acids G at position 1 and/or S at position 2 of SEQ ID NO:1 to 3 can be removed from N-terminal ankyrin capping modules without any apparent influence on the properties. These two amino acids serve as linkers to connect the ankyrin repeat domain to further amino acids and proteins. The invention also comprises such ankyrin repeat domains comprising N-terminal ankyrin capping modules wherein G at position 1 and/or S at position 2 are removed. It is understood that the amino acid positions (e.g. "position 33") in an ankyrin repeat domain as defined herein are adapted accordingly, resulting in a number shift, e.g. "position 33" will become "position 32", if one amino acid is missing, or "position 33" will become "position 31", if two amino acid are missing.

An ankyrin capping module of an ankyrin repeat domain of the invention can be exchanged by an ankyrin capping module by combining techniques, such as alignment of amino acid sequences, mutagenesis and gene synthesis, known to the person skilled in the art. For example, the C-terminal capping repeat of SEQ ID NO:49 can be replaced by the C-terminal capping repeat of SEQ ID NO:8 by (i) determination of the C-terminal capping repeat of SEQ ID NO:49 (i.e. sequence position 132 to 159) by sequence alignment with SEQ ID NO:8, (ii) replacing the sequence of the determined C-terminal capping repeat of SEQ ID NO:49 with the sequence of SEQ ID NO:8, (iii) generation of a gene encoding the repeat domain encoding the exchanged C-terminal capping module, (iv) expressing of the modified repeat domain in the cytoplasm of E. coli and (v) purification of the modified repeat domain by standard means. As a further example, the N-terminal capping repeat of SEQ ID NO:49 can be replaced by the N-terminal capping repeat of SEQ ID NO:2 by (i) determination of the N-terminal capping repeat of SEQ ID NO:49 (i.e. sequence position 1 to 32) by sequence alignment with SEQ ID NO:2, (ii) replacing the sequence of the determined N-terminal capping repeat of SEQ ID NO:49 with the sequence of SEQ ID NO:2, (iii) generation of a gene encoding the repeat domain encoding the exchanged N-terminal capping module, (iv) expressing of the modified repeat domain in the cytoplasm of E. coli and (v) purification of the modified repeat domain by standard means.

Furthermore, an ankyrin repeat domain of the invention can be constructed genetically by assembling a N-terminal ankyrin capping module (e.g. the N-terminal capping repeat of SEQ ID NO:2) followed by one or more repeat modules (e.g. the three ankyrin repeat modules comprising the amino acid residues from position 33 to 131 of SEQ ID NO:49) and a C-terminal capping module (e.g. the C-terminal capping repeat of SEQ ID NO:8) by means of gene synthesis. The genetically assembled repeat domain gene can then be expressed in E. coli as described above.

Further preferred is a recombinant binding protein, repeat domain, repeat module, N-terminal capping module or C-terminal capping module having an amino acid sequence devoid of amino acids C, M or N.

Further preferred is a recombinant binding protein, repeat domain, repeat module, N-terminal capping module or C-terminal capping module having an amino acid sequence devoid of amino acid N followed by G.

Further preferred is a recombinant binding protein or repeat domain comprising any such N-terminal or C-terminal capping module.

In a further preferred embodiment of a recombinant binding protein comprising an ankyrin repeat domain according to the present invention, one or more of the amino acid residues of the N-terminal capping module of said repeat domain is exchanged by an amino acid residue found at the corresponding position on alignment of an N-terminal capping unit. Preferably, up to 30% of the amino acid residues are exchanged, more preferably, up to 20%, and even more preferably, up to 10% of the amino acid residues are exchanged. Most preferably, such an N-terminal capping unit is a naturally occurring N-terminal capping unit.

In a further preferred embodiment of a recombinant binding protein comprising an ankyrin repeat domain according to the present invention, one or more of the amino acid residues of the C-terminal capping module of said repeat domain is exchanged by an amino acid residue found at the corresponding position on alignment of a C-terminal capping unit. Preferably, up to 30% of the amino acid residues are exchanged, more preferably, up to 20%, and even more preferably, up to 10% of the amino acid residues are exchanged. Most preferably, such a C-terminal capping unit is a naturally occurring C-terminal capping unit.

In still another particular embodiment, up to 30% of the amino acid residues, more preferably, up to 20%, and even more preferably, up to 10% of the amino acid residues are exchanged with amino acids which are not found in the corresponding positions of repeat units, N-terminal capping units or C-terminal capping units.

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

Further preferred are non-naturally occurring capping modules, repeat modules, binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

In one particular embodiment the invention relates to a recombinant binding protein comprising an ankyrin repeat domain specifically binding to PDGF-BB and further comprising an ankyrin repeat domain specifically binding to vascular endothelial growth factors A (VEGF-A). Examples of ankyrin repeat domains with specificity for PDGF-BB are given herein and examples of ankyrin repeat domains with specificity to VEGF-A are described in WO 2010/060748 (US 2011/0207668) and WO 2011/135067 (US 2013/0116197), the entire disclosures of which are incorporated by reference herein. Such two repeat domains can be linked by a polypeptide linker by genetic means by methods known to the person skilled in the art. In one embodiment of the invention, a recombinant binding protein comprising an ankyrin repeat domain specifically binding PDGF-BB and an ankyrin repeat domain specifically binding VEGF-A may be used to treat diseases of the retina and choroidal neovascular diseases, such as exudative age-related macular degeneration, polypoidal choroidal neovascularization, and pathological myopia.

Another preferred embodiment is a recombinant binding protein comprising an ankyrin repeat domain with binding specificity for PDGF-BB comprising one, two, three or more internal repeat modules that will participate in binding to PDGF-BB. Preferably, such an ankyrin repeat domain comprises an N-terminal capping module, two to four internal repeat modules, and a C-terminal capping module. Preferably, said capping modules are capping repeats. Also preferably, said capping modules will participate in binding to PDGF-BB.

Further preferred is a recombinant binding protein comprising two or more of said ankyrin repeat domains with binding specificity for PDGF-BB. Preferably, said binding protein comprises 2 or 3 of said repeat domains. Said two or more repeat domains have the same or different amino acid sequence.

In a further preferred embodiment of a recombinant binding protein comprising an ankyrin repeat domain according to the present invention, one or more of the amino acid residues of the repeat modules of said ankyrin repeat domain are exchanged by an amino acid residue found at the corresponding position on alignment of a repeat unit. Preferably, up to 30% of the amino acid residues are exchanged, more preferably, up to 20%, and even more preferably, up to 10% of the amino acid residues are exchanged. Most preferably, such a repeat unit is a naturally occurring repeat unit.

In still another particular embodiment, up to 30% of the amino acid residues, for example 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0% of the amino acid residues are exchanged with amino acids which are not found in the corresponding positions of repeat units. More preferably, up to 20%, and even more preferably, up to 10% of the amino acid residues are exchanged with amino acids which are not found in the corresponding positions of repeat units.

In further embodiments, any of the recombinant PDGF-BB binding proteins or domains described herein may be covalently bound to one or more additional moieties, including, for example, a moiety that binds to a different target to create a dual-specificity binding agent, a bioactive compound, a labeling moiety (e.g. a fluorescent label such as fluorescein, or a radioactive tracer), a moiety that facilitates protein purification (e.g. a small peptide tag, such as a His- or strep-tag), a moiety that provides effector functions for improved therapeutic efficacy (e.g. the Fc part of an antibody to provide antibody-dependent cell-mediated cytotoxicity, a toxic protein moiety such as *Pseudomonas aeruginosa* exotoxin A (ETA) or a small molecular toxic agent such as maytansinoids or DNA alkylating agents) or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein between the concentration shortly after administration and the concentration shortly before the next administration). Moieties that tend to slow clearance of a protein from the blood include hydroxyethyl starch (HES), polyethylene glycol (PEG), sugars (e.g. sialic acid), well-tolerated protein moieties (e.g. Fc fragments or serum albumin), and binding domains or peptides with specificity and affinity for abundant serum proteins, such as antibody Fc fragments or serum albumin. Examples of such binding domains with affinity for serum albumin are provided in WO 2012/069654. The recombinant binding protein of the invention may be attached to a moiety that reduces the clearance rate of polypeptides in a mammal (e.g. in mouse, rat, or human) by greater than three-fold relative to the unmodified polypeptides.

In a further embodiment, the invention relates to nucleic acid molecules encoding the particular recombinant binding proteins, the particular ankyrin repeat domains, the particular ankyrin repeat modules and the particular capping modules. Further, a vector comprising said nucleic acid molecule is considered.

Further, a pharmaceutical composition comprising one or more of the above mentioned recombinant binding proteins, in particular binding proteins comprising repeat domains, or nucleic acid molecules encoding the particular binding proteins, and optionally a pharmaceutical acceptable carrier and/or diluent is considered. Pharmaceutical acceptable carriers and/or diluents are known to the person skilled in the art and are explained in more detail below. Even further, a diagnostic composition comprising one or more of the above mentioned recombinant binding proteins, in particular binding proteins comprising repeat domains, is considered.

A pharmaceutical composition comprises recombinant binding proteins as described above and a pharmaceutically acceptable carrier, excipient or stabilizer, for example as described in Remington's Pharmaceutical Sciences 16$^{th}$ edition, Osol, A. Ed. [1980]. Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent.

The formulations to be used for in vivo administration must be aseptic or sterile. This is readily accomplished by filtration through sterile filtration membranes.

The pharmaceutical composition may be administered by any suitable method within the knowledge of the person skilled in the art.

Further, any of the above mentioned pharmaceutical composition is considered for the treatment of a disorder.

The invention further provides methods of treatment. The method comprises administering, to a patient in need thereof, a therapeutically effective amount of a recombinant binding protein of the invention, that is, an amount that is sufficient to produce a desired effect on a patient.

Further, a method of treating a pathological condition in a mammal including man, comprising administering to a patient in need thereof an effective amount of the above mentioned pharmaceutical composition is considered.

Examples of such pathological conditions are atherosclerosis, restenosis, pulmonary hypertension, ocular and retinal diseases and fibrotic diseases, including pulmonary fibrosis, liver cirrhosis, scleroderma, glomerulosclerosis and cardiac fibrosis. In addition, anti-PDGF-BB therapy is useful for oncology pathological conditions, such as gliomas, sarcomas, leukemias, lymphomas and epithelial cancers.

The recombinant binding protein or ankyrin repeat domain according to the invention may be obtained and/or further evolved by several methods such as display on the surface of bacteriophages (WO 1990/002809, WO 2007/006665) or bacterial cells (WO 1993/010214), ribosomal display (WO 1998/048008), display on plasmids (WO 1993/008278) or by using covalent RNA-repeat protein hybrid constructs (WO 2000/032823), or intracellular expression and selection/screening such as by protein complementation assay (WO 1998/341120). Such methods are known to the person skilled in the art.

A library of ankyrin repeat proteins used for the selection/screening of a recombinant binding protein or ankyrin repeat domain according to the invention may be obtained according to protocols known to the person skilled in the art (WO 2002/020565, Binz, H. K., et al., J. Mol. Biol., 332, 489-503, 2003, and Binz et al., 2004, loc. cit). The use of such libraries for the selection of ankyrin repeat domains with specificity for PDGF-BB is exemplified in Example 1. Furthermore, ankyrin repeat domains of the present invention may be modularly assembled from ankyrin repeat modules according to the current invention and appropriate capping modules or capping repeats (Forrer, P., et al., FEBS letters 539, 2-6, 2003) using standard recombinant DNA technologies (e.g. WO 2002/020565, Binz et al., 2003, loc. cit. and Binz et al., 2004, loc. cit).

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.
Materials Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *E. coli* XL1-blue (Stratagene, USA) or BL21 (Novagen, USA). Recombinant human and murine PDGF-BB was purchased from Reliatech (Germany; product numbers 200-055 and M10-125, respectively). Biotinylated PDGF-BB was obtained chemically via coupling of the biotin moiety to primary amines of the protein using standard biotinylation reagents and methods (Pierce, USA).
Molecular Biology Unless stated otherwise, methods are performed according to described protocols (Sambrook J., Fritsch E. F. and Maniatis T., Molecular Cloning: A Laboratory Manual, Cold Spring Harbor Laboratory 1989, New York).
Designed Ankyrin Repeat Protein Libraries Methods to generate designed ankyrin repeat protein libraries are described (WO 2002/020565; Binz et al. 2003, loc. cit.; Binz et al. 2004, loc. cit.). By such methods designed ankyrin repeat protein libraries having randomized ankyrin repeat modules and/or randomized capping modules can be constructed. For example, such libraries could accordingly be assembled based on a fixed N-terminal capping module (e.g. the N-terminal capping module of SEQ ID NO: 2) or a randomized N-terminal capping module according to SEQ ID NO: 64, one or more randomized repeat modules according to the sequence motif of SEQ ID NO: 20, 62 or 63, and a fixed C-terminal capping module (e.g. the C-terminal capping module of SEQ ID NO: 8) or a randomized C-terminal capping module according to SEQ ID NO: 65. Preferably, such libraries are assembled to not have the amino acids C, G, M, N (in front of a G residue) or P at randomized positions of repeat or capping modules. In addition, randomized repeat modules according to the sequence motif of SEQ ID NO: 20, 62 or 63 could be further randomized at position 10 and/or position 17; the randomized N-terminal capping module according to the sequence motif of SEQ ID NO: 64 could be further randomized at position 7 and/or position 9; and the randomized C-terminal capping modules according to the sequence motif of SEQ ID NO: 65 could be further randomized at positions 10, 11 and/or 17.

Furthermore, such randomized modules in such libraries may comprise additional polypeptide loop insertions with randomized amino acid positions. Examples of such polypeptide loop insertions are complement determining region (CDR) loop libraries of antibodies or de novo generated peptide libraries. For example, such a loop insertion could be designed using the structure of the N-terminal ankyrin repeat domain of human ribonuclease L (Tanaka, N., Nakanishi, M, Kusakabe, Y, Goto, Y., Kitade, Y, Nakamura, K. T., EMBO J. 23(30), 3929-3938, 2004) as guidance. In analogy to this ankyrin repeat domain where ten amino acids are inserted in the beta-turn present close to the boarder of two ankyrin repeats, ankyrin repeat proteins libraries may contain randomized loops (with fixed and randomized positions) of variable length (e.g. 1 to 20 amino acids) inserted in one or more beta-turns of an ankyrin repeat domain.

Any such N-terminal capping module of an ankyrin repeat protein library preferably possesses the RELLKA or RILKAA motif instead of the RILLAA motif (e.g. present from position 21 to 26 in SEQ ID NO:64) and any such C-terminal capping module of an ankyrin repeat protein library preferably possesses the KAA or KLA motif instead of the KLN motif (e.g. the last three amino acids in SEQ ID NO:65).

The design of such an ankyrin repeat protein library may be guided by known structures of an ankyrin repeat domain interacting with a target. Examples of such structures, identified by their Protein Data Bank (PDB) unique accession or identification codes (PDB-IDs), are 1WDY, 3V31, 3V30, 3V2X, 3V20, 3UXG, 3TWQ-3TWX, 1N11, 1S70 and 2ZGD.

Examples of designed ankyrin repeat protein libraries, such as the N2C and N3C designed ankyrin repeat protein libraries, are described (WO 2002/020565; Binz et al. 2003, loc. cit.; Binz et al. 2004, loc. cit.). The digit in N2C and N3C describes the number of randomized repeat modules present between the N-terminal and C-terminal capping modules.

The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of a ankyrin repeat module of the current disclosure and consequently position 33 of a ankyrin repeat module of Binz et al.

2004, loc. cit. corresponds to position 1 of a following ankyrin repeat module of the current disclosure.

All the DNA sequences were confirmed by sequencing, and the calculated molecular weight of all described proteins was confirmed by mass spectrometry.

Example 1

Selection of Binding Proteins Comprising an Ankyrin Repeat Domain with Binding Specificity for PDGF-BB Using ribosome display (Hanes, J. and Plückthun, A., PNAS 94, 4937-42, 1997) many designed ankyrin repeat proteins (DARPins) with binding specificity for PDGF-BB were selected from DARPin libraries as described by Binz et al. 2004 (loc. cit.). The binding of the selected clones toward specific (PDGF-BB) and unspecific (MBP, E. coli maltose binding protein) targets was assessed by crude extract ELISA indicating that hundreds PDGF-BB binding proteins were successfully selected. For example, the ankyrin repeat domains of SEQ ID NO: 23 to 61 constitute amino acid sequences of selected binding proteins comprising an ankyrin repeat domain with binding specificity for PDGF-BB. Individual ankyrin repeat modules from such ankyrin repeat domains with binding specificity to PDGF-BB are provided in SEQ ID NO: 12, 14, 15, 17, 18 and 19. Individual capping modules of such ankyrin repeat domains with binding specificity to PDGF-BB are provided in SEQ ID NO: 13 and 16.

Selection of PDGF-BB Specific Ankyrin Repeat Proteins by Ribosome Display

The selection of PDGF-BB specific ankyrin repeat proteins was performed by ribosome display (Hanes and Plückthun, loc. cit.) using human and mouse PDGF-BB as target proteins, libraries of designed ankyrin repeat proteins as described above and established protocols (Zahnd, C., Amstutz, P. and Plückthun, A., Nat. Methods 4, 69-79, 2007). The number of reverse transcription (RT)-PCR cycles after each selection round was constantly reduced from 40 to 30, adjusting to the yield due to enrichment of binders. The first four rounds of selection employed standard ribosome display selection, using decreasing target concentration and increasing washing stringency to increase selection pressure from round 1 to round 4 (Binz et al. 2004, loc. cit.). To enrich high affinity anti-PDGF-BB DARPins, the output from the fourth round of standard ribosome display selection (above) was subjected to an off-rate selection round with increased selection stringency (Zahnd, 2007, loc. cit.). A final standard selection round was performed to amplify and recover the off-rate selected binding proteins.

Selected Clones Bind Specifically to PDGF-BB as Shown by Crude Extract ELISA

Individual selected DARPins specifically binding PDGF-BB were identified by an enzyme-linked immunosorbent assay (ELISA) using crude Escherichia coli extracts of DARPin expression cells using standard protocols. DARPins selected by ribosome display were cloned into the pQE30 (Qiagen) expression vector, transformed into E. coli XL1-Blue (Stratagene) and then grown overnight at 37° C. in a 96-deep-well plate (each clone in a single well) containing 1 ml growth medium (2YT containing 1% glucose and 100 µg/ml ampicillin). 1 ml of fresh 2YT containing 50 µg/ml ampicillin was inoculated with 100 µl of the overnight culture in a fresh 96-deep-well plate. After incubation for 2 h at 37° C., expression was induced with IPTG (1 mM final concentration) and continued for 3 h. Cells were harvested, resuspended in 100 µl B-PERII (Pierce) and incubated for 15 min at room temperature with shaking. Then, 900 µl PBS-TC (PBS supplemented with 0.25% Casein hydrolysate, 0.1% Tween 20®, pH 7.4) were added and cell debris were removed by centrifugation. 100 µl of each lysed clone were applied to a well of a Neutravidin coated MaxiSorp plate containing either PDGF-BB or the unrelated MBP immobilized via their biotin moiety and incubated for 1 h at RT. After extensive washing with PBS-T (PBS supplemented with 0.1% Tween 20®, pH 7.4) the plate was developed using standard ELISA procedures using the monoclonal horse-radish-labeled anti-RGS(His)$_4$ antibody (34650, Qiagen) Binding was then detected by POD substrate (Roche). The color development was measured at 405 nm. Screening of several hundred clones by such a crude cell extract ELISA revealed more than hundred different DARPins with specificity for PDGF-BB. These binding proteins were chosen for further analysis. Examples of amino acid sequences of selected ankyrin repeat domains that specifically bind to PDGF-BB are provided in SEQ ID NO:23 to 61.

These ankyrin repeat domains with binding specificity for PDGF-BB and negative control DARPins with no binding specificity for PDGF-BB (i.e. DARPin #21 and #22) were cloned into a pQE (QIAgen, Germany) based expression vector providing an N-terminal His-tag to facilitate simple protein purification as described below. Thus, expression vectors encoding the following DARPins were constructed:

DARPin #21 (SEQ ID NO:21 with a His-tag (SEQ ID NO:9) fused to its N-terminus);
DARPin #22 (SEQ ID NO:22 with a His-tag (SEQ ID NO:9) fused to its N-terminus);
DARPin #23 (SEQ ID NO:23 with a His-tag (SEQ ID NO:9) fused to its N-terminus);
DARPin #24 (SEQ ID NO:24 with a His-tag (SEQ ID NO:9) fused to its N-terminus);
DARPin #25 (SEQ ID NO:25 with a His-tag (SEQ ID NO:9) fused to its N-terminus);
DARPin #26 (SEQ ID NO:26 with a His-tag (SEQ ID NO:9) fused to its N-terminus);
DARPin #27 (SEQ ID NO:27 with a His-tag (SEQ ID NO:9) fused to its N-terminus);
DARPin #28 (SEQ ID NO:28 with a His-tag (SEQ ID NO:9) fused to its N-terminus);
DARPin #29 (SEQ ID NO:29 with a His-tag (SEQ ID NO:9) fused to its N-terminus);
DARPin #30 (SEQ ID NO:30 with a His-tag (SEQ ID NO:9) fused to its N-terminus);
DARPin #31 (SEQ ID NO:31 with a His-tag (SEQ ID NO:9) fused to its N-terminus);
DARPin #32 (SEQ ID NO:32 with a His-tag (SEQ ID NO:9) fused to its N-terminus);
DARPin #33 (SEQ ID NO:33 with a His-tag (SEQ ID NO:9) fused to its N-terminus);
DARPin #34 (SEQ ID NO:34 with a His-tag (SEQ ID NO:9) fused to its N-terminus);
DARPin #35 (SEQ ID NO:35 with a His-tag (SEQ ID NO:9) fused to its N-terminus);
DARPin #36 (SEQ ID NO:36 with a His-tag (SEQ ID NO:9) fused to its N-terminus);
DARPin #37 (SEQ ID NO:37 with a His-tag (SEQ ID NO:9) fused to its N-terminus);
DARPin #38 (SEQ ID NO:38 with a His-tag (SEQ ID NO:9) fused to its N-terminus);
DARPin #39 (SEQ ID NO:39 with a His-tag (SEQ ID NO:9) fused to its N-terminus);
DARPin #40 (SEQ ID NO:40 with a His-tag (SEQ ID NO:9) fused to its N-terminus);

DARPin #41 (SEQ ID NO:41 with a His-tag (SEQ ID NO:9) fused to its N-terminus);
DARPin #42 (SEQ ID NO:42 with a His-tag (SEQ ID NO:9) fused to its N-terminus);
DARPin #43 (SEQ ID NO:43 with a His-tag (SEQ ID NO:9) fused to its N-terminus);
DARPin #44 (SEQ ID NO:44 with a His-tag (SEQ ID NO:9) fused to its N-terminus);
DARPin #45 (SEQ ID NO:45 with a His-tag (SEQ ID NO:9) fused to its N-terminus);
DARPin #46 (SEQ ID NO:46 with a His-tag (SEQ ID NO:9) fused to its N-terminus);
DARPin #47 (SEQ ID NO:47 with a His-tag (SEQ ID NO:9) fused to its N-terminus);
DARPin #48 (SEQ ID NO:48 with a His-tag (SEQ ID NO:9) fused to its N-terminus);
DARPin #49 (SEQ ID NO:49 with a His-tag (SEQ ID NO:9) fused to its N-terminus);
DARPin #50 (SEQ ID NO:50 with a His-tag (SEQ ID NO:9) fused to its N-terminus);
DARPin #51 (SEQ ID NO:51 with a His-tag (SEQ ID NO:9) fused to its N-terminus);
DARPin #52 (SEQ ID NO:52 with a His-tag (SEQ ID NO:9) fused to its N-terminus);
DARPin #53 (SEQ ID NO:53 with a His-tag (SEQ ID NO:9) fused to its N-terminus);
DARPin #54 (SEQ ID NO:54 with a His-tag (SEQ ID NO:9) fused to its N-terminus);
DARPin #55 (SEQ ID NO:55 with a His-tag (SEQ ID NO:9) fused to its N-terminus);
DARPin #56 (SEQ ID NO:56 with a His-tag (SEQ ID NO:9) fused to its N-terminus);
DARPin #57 (SEQ ID NO:57 with a His-tag (SEQ ID NO:9) fused to its N-terminus);
DARPin #58 (SEQ ID NO:58 with a His-tag (SEQ ID NO:9) fused to its N-terminus);
DARPin #59 (SEQ ID NO:59 with a His-tag (SEQ ID NO:9) fused to its N-terminus);
DARPin #60 (SEQ ID NO:60 with a His-tag (SEQ ID NO:9) fused to its N-terminus);
DARPin #61 (SEQ ID NO:61 with a His-tag (SEQ ID NO:9) fused to its N-terminus);

High Level and Soluble Expression of DARPins

For further analysis, the selected clones showing specific PDGF-BB binding in the crude cell extract ELISA as described above were expressed in *E. coli* BL21 or XL1-Blue cells and purified using their His-tag using standard protocols. 50 ml of stationary overnight cultures (TB, 1% glucose, 100 mg/l of ampicillin; 37° C.) were used to inoculate 1 l cultures (same medium without glucose). At an absorbance of 0.7 (1 for BL21) at 600 nm, the cultures were induced with 0.5 mM IPTG and incubated at 37° C. for 4-5 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Alternatively, DARPins or selected repeat domains devoid of a 6×His-tag were purified by anion exchange chromatography followed by size exclusion chromatography according to standard resins and protocols known to the person skilled in the art. Up to 200 mg of highly soluble DARPins with binding specificity to PDGF-BB can be purified from one liter of *E. coli* culture with a purity >95% as estimated from SDS-15% PAGE. Such purified DARPins are used for further characterizations.

Example 2

Characterization of the DARPins with Binding for Specificity for PDGF-BB by Surface Plasmon Resonance Analysis Biotinylated PDGF-BB molecules from human and mouse were immobilized in a flow cell through binding to coated Streptavidin and the interaction with various selected DARPins was analyzed.

Surface Plasmon Resonance (SPR) Analysis

SPR was measured using a ProteOn instrument (BioRad) and measurement was performed according standard procedures known to the person skilled in the art. The running buffer was PBS, pH 7.4, containing 0.005% Tween 20®. Neutravidin was covalently immobilized on a GLC chip (Bio-Rad) to a level of about 8000 resonance units (RU). Immobilization of PDGF-BB on the neutravidin coated chip was then performed. The interaction of DARPin PDGF-BB was then measured by injecting 100 µl running buffer (PBS containing 0.005% Tween®) containing serial dilutions of DARPins of concentration of 12.5, 6.26, 3.13 and 1.67 nM (on-rate measurement), followed by a running buffer flow for between 10 minutes and up to 3 hours at a constant flow rate of 30 µl/min (off-rate measurement). The signals (i.e. resonance unit (RU) values) of an uncoated reference cell and a reference injection (i.e. injection of running buffer only) were subtracted from the RU traces obtained after injection of PDGF-BB (double-referencing). From the SRP traces obtained from the on-rate and off-rate measurements the on- and off-rate of the corresponding DARPin PDGF-BB interaction can be determined.

The results are summarized in Table 1. Dissociation constants (Kd) were calculated from the estimated on- and off-rates using standard procedures known to the person skilled in the art.

TABLE 1

Dissociation constants of DARPin PDGF-BB interactions (human and mouse) determined by SPR

| DARPin# | Kd [M] (human) | Kd [M] (mouse) |
| --- | --- | --- |
| 23 | 2.14E−11 | 1.72E−11 |
| 24 | 3.01E−11 | n.d. |
| 25 | 1.47E−11 | 1.28E−11 |
| 26 | 1.77E−11 | 1.74E−11 |
| 28 | 1.71E−11 | n.d. |
| 29 | 1.05E−10 | n.d. |
| 30 | 1.10E−10 | n.d. |
| 31 | 1.09E−10 | n.d. |
| 32 | 6.38E−11 | 8.34E−11 |
| 33 | 8.06E−11 | 9.04E−11 |
| 34 | 7.75E−11 | 5.92E−11 |
| 35 | 9.56E−11 | 9.81E−11 |
| 36 | 2.42E−11 | 5.30E−11 |
| 37 | 1.52E−10 | 8.28E−11 |
| 38 | 9.41E−11 | 5.83E−11 |
| 39 | 1.72E−10 | 3.82E−10 |
| 40 | 3.44E−11 | 6.08E−11 |
| 42 | 8.05E−11 | 9.74E−11 |
| 43 | 1.29E−06 | 1.51E−06 |
| 44 | 7.68E−11 | 9.02E−11 |
| 45 | 1.08E−10 | n.d. |
| 46 | 1.12E−10 | n.d. |
| 47 | 9.37E−11 | n.d. |
| 48 | 1.13E−10 | 1.21E−10 |
| 49 | 7.69E−11 | 1.02E−10 |
| 50 | 1.15E−10 | n.d. |

TABLE 1-continued

Dissociation constants of DARPin PDGF-BB interactions (human and mouse) determined by SPR

| DARPin# | Kd [M] (human) | Kd [M] (mouse) |
|---|---|---|
| 51 | 1.21E−10 | n.d. |
| 53 | 1.28E−10 | n.d. |
| 54 | 2.45E−10 | n.d. |
| 55 | 5.55E−11 | n.d. |
| 56 | 1.50E−10 | n.d. |
| 57 | 1.23E−10 | n.d. |
| 58 | 2.57E−10 | n.d. |
| 59 | 1.71E−10 | n.d. | n.d.: not determined.

Example 3

Inhibition of Fibroblast Proliferation by DARPins with Binding Specificity for PDGF-BB NIH-3T3 fibroblast cells are a standard cell line used for assays involving PDGF-BB. On day 1 at 70%-80% confluence, the cells were harvested and seeded in a 96-well culture plate with density of 5000 cells/well in a growth medium, followed by starving of cells around 7-8 hours later by changing of medium to assay medium and incubated for 24 hours. All incubation condition was 37° C. with 5% $CO_2$ flow. Following the starving of cells, on day 2 the media was changed into a fresh assay media containing the dilution series of growth factor human PDGF-BB (for the proliferation assay) or a inhibition mixture of 20 ng/mL human PDGF-BB with a 2.5-fold dilution series of DARPins (200 nM to 0.05 nM) for the inhibition assay. The cells were incubated for another 48 h in this condition upon the addition of 20 μL of WST-1 reagent (Roche product no. 11644807001). This reagent enables a colorimetric assay that analyzes the number of viable cells. Readout of the signals was done at $A_{450}$ nm with a correction background at $A_{600}$ nm at several time points of 2, 4 and 6 hours after the addition of WST-1.

Figure 1:
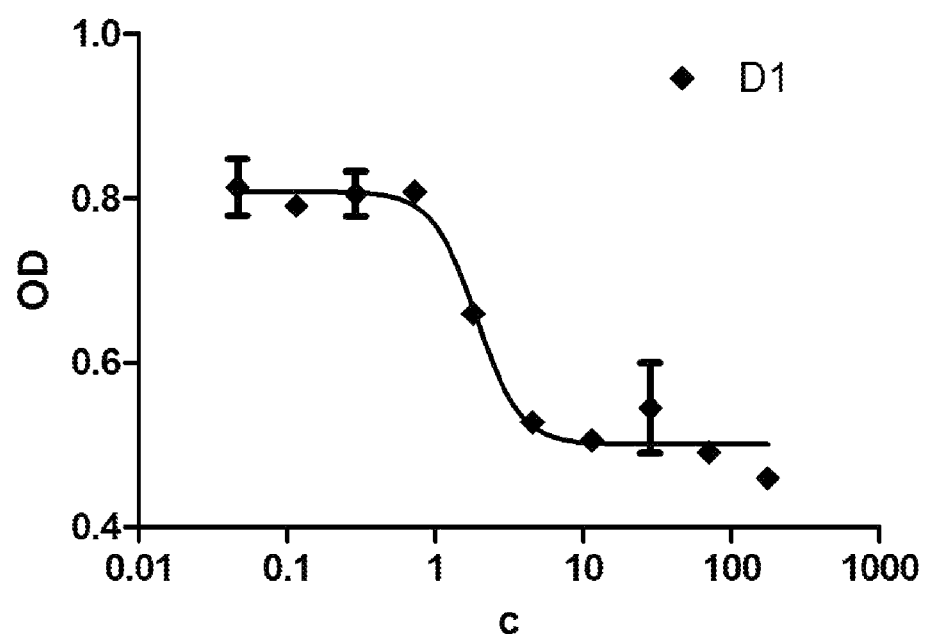
FIG. 1. Inhibition of NHI-3T3 fibroblast proliferation
Inhibition of proliferation of NIH-3T3 fibroblasts by various concentrations of a DARPin with specificity for PDGF-BB (exemplified by DARPin #49) and a corresponding fitted inhibition curve are shown. The $IC_{50}$ value was then calculated from the fitted inhibition curve to be 1.9 nM for DARPin #49.

Example results are summarized in Table 2. $IC_{50}$ values were calculated from the titration curves obtained as described above using GraphPad Prism software and standard procedures known to the person skilled in the art. An example titration curve is given for DARPin #49 in FIG. 1.

TABLE 2

Inhibition potency by various DARPins of NIH-3T3 cell proliferation induced by PDGF-BB

| DARPin# | $IC_{50}$ [nM] |
|---|---|
| 24 | 1.4 |
| 28 | 1.6 |
| 30 | 3.2 |
| 49 | 1.9 |
| 59 | 2.0 |

Example 4

Characterization of DARPins with Binding Specificity for PDGF-BB by Receptor Competition Assay The potency of PEGylated anti-PDGF-BB DARPins to inhibit the binding of human PDGF-BB to its receptor PDGFRbeta was determined in a in a receptor competition ELISA (based on PDGF-BB Quantikine, R&D Systems). PDGFR-beta/Fc chimera has been precoated on a microplate. The DARPins were preincubated in assay diluent from the PDGF-BB Quantikine kit (R&D Systems) with a defined amount of PDGF-BB and incubated at room temperature for 2 hours with shaking at 750 rpm. These preincubation mixtures were then transferred into the precoated wells and any PDGF-BB that is not blocked by the DARPins was bound by the immobilized receptor. After washing away any unbound substances, a horse radish peroxidase-linked polyclonal antibody specific for PDGF-BB was added to the wells. Following a wash to remove any unbound antibody-enzyme reagent, a substrate solution was added to the wells and color was developing in proportion to the amount of PDGF-BB bound. The color development was stopped and the intensity of the color was measured at 405 nm. In this assay, the tested DARPins showed high PDGF-BB inhibition potency as summarized in Table 3. Example titration curves are given for a set of DARPins in FIG. 2. $IC_{50}$ values were calculated from such titration curves obtained as described above using Graph Pad Prism software and standard procedures known to the person skilled in the art.

TABLE 3

Inhibition of the PDGF-BB interaction with its receptor PDGFRbeta by DARPins (mean $IC_{50}$ values are given)

| DARPin# | $IC_{50}$ [pM] |
|---|---|
| 23 | 22 |
| 24 | 15 |
| 28 | 16 |
| 29 | 15 |
| 30 | 490 |
| 31 | 480 |
| 34 | 210 |
| 37 | >400 |
| 38 | 85 |
| 44 | 130 |
| 45 | 160 |
| 46 | 150 |
| 47 | 140 |
| 49 | 66 |
| 50 | 32 |
| 51 | 8 |
| 52 | 68 |
| 53 | 36 |
| 54 | 210 |
| 55 | 14 |
| 56 | 170 |
| 57 | 204 |
| 58 | 470 |

Example 5

Inhibition of Laser-Induced Choroidal Neovascularization in Mouse by DARPins with Binding Specificity for PDGF-BB The effect on the growth of neovessels was tested in vivo. A mouse laser choroidal neovascularization model was chosen and performed as published described (Takahashi, K., Saishin, Y., Saishin, Y., King, A. G., Levin, R. and Campochiaro, P. A., Arch. Ophthalmol. 127(4), 494-499, 2009). Choroidal neovascularization (CNV) was induced by laser photocoagulation-induced rupture of Bruch's membrane as previously described. On day 2, adult C57BL/6 mice were anesthetized with ketamine hydrochloride (100 mg/kg body weight), and pupils were dilated with 1% tropicamide. Three burns of 532 nm diode laser photocoagulation (75 μm spot size, 0.1 seconds duration, 120 mW) were delivered to each retina with the slit lamp delivery system of an OcuLight GL diode laser using a handheld cover slip as a contact lens to view the retina. Burns were performed in the 9, 12, and 3 o'clock positions of the posterior pole of the retina. Production of a bubble at the time of laser, which indicates rupture of Bruch's membrane, is an important factor in obtaining choroidal neovascularization, and therefore, only burns in which a bubble was produced were included in the study. DARPin #61-PEG20 was administered daily with a concentration of 10 or 1 mg/kg, respectively, as indicated in FIG. 3. On day 14, mice were heart perfused with fluorescein-labeled dextran, retinal flat-mounts were prepared as described (Takahashi et al., loc cit) and the area of neovascularization was quantified by image analysis. Statistical analysis was performed using 1-way ANOVA and Dunnett post-test to compare all DARPin groups to the vehicle group. These techniques are all known to persons skilled in the art. The results are presented in FIG. 3.

The invention claimed is:

1. A recombinant binding protein comprising at least one ankyrin repeat domain, wherein said ankyrin repeat domain specifically binds PDGF-BB and wherein said ankyrin repeat domain comprises an ankyrin repeat module having an amino acid sequence selected from the group consisting of SEQ ID NO: 12, 14, 15, 17, 18 and 19 and sequences, wherein (1) up to 6 amino acids in SEQ ID NO:12 are exchanged by another amino acid, wherein the up to 6 amino acid exchanges are:
E at position 3 is optionally exchanged by an amino acid selected from the group consisting of D, W, Q, I and Y;
E at position 4 is optionally exchanged by an amino acid selected from the group consisting of T, D, Y, and S;
T at position 6 is optionally exchanged by an amino acid selected from the group consisting of S and F;
Y at position 11 is optionally exchanged by F;
V at position 14 is optionally exchanged by an amino acid selected from the group consisting of A, Y and T; and
W at position 15 is optionally exchanged by an amino acid selected from the group consisting of F, K, V, and Y; or (2) up to 6 amino acids in SEQ ID NO:15 are exchanged by another amino acid, wherein the up to 6 amino acid exchanges are:
Q at position 3 is optionally exchanged by A;
E at position 4 is optionally exchanged by D;
T at position 6 is optionally exchanged by E;
F at position 11 is optionally exchanged by Y;
S at position 14 is optionally exchanged by V; and
V at position 15 is optionally exchanged by W; or (3) up to 2 amino acids in SEQ ID NO:17 are exchanged by another amino acid, wherein the up to 2 amino acid exchanges are:
K at position 1 is optionally exchanged by Q or I; and
L at position 3 is optionally exchanged by N; or (4) up to 3 amino acids in SEQ ID NO:18 are exchanged by another amino acid, wherein the up to 3 amino acid exchanges are:

K at position 1 is optionally exchanged by Q;
W at position 14 is optionally exchanged by H; and
A at position 15 is optionally exchanged by V; or (5) up to 4 amino acids in SEQ ID NO:19 are exchanged by another amino acid, wherein the up to 4 amino acid exchanges are:
K at position 1 is optionally exchanged by N;
A at position 12 is optionally exchanged by T;
A at position 13 is optionally exchanged by T; and
E at position 22 is optionally exchanged by D.

2. The recombinant binding protein of claim 1, wherein said ankyrin repeat module has the amino acid sequence KDEEGTTPLHYAAVWGHLEIVEVLLKAGADVNA (SEQ ID NO:12).

3. The recombinant binding protein of claim 1, wherein said ankyrin repeat module has the amino acid sequence KDEEGTTPLHYAAVWGHLEIVEVLLKAGADVNA (SEQ ID NO:12), wherein up to 6 amino acids in SEQ ID NO:12 are exchanged by another amino acid, wherein the up to 6 amino acid exchanges are:
E at position 3 is optionally exchanged by an amino acid selected from the group consisting of D, W, Q, I and Y;
E at position 4 is optionally exchanged by an amino acid selected from the group consisting of T, D, Y, and S;
T at position 6 is optionally exchanged by an amino acid selected from the group consisting of S and F;
Y at position 11 is optionally exchanged by F;
V at position 14 is optionally exchanged by an amino acid selected from the group consisting of A, Y and T; and
W at position 15 is optionally exchanged by an amino acid selected from the group consisting of F, K, V, and Y.

4. The recombinant binding protein of claim 1, wherein said ankyrin repeat module has the amino acid sequence KDKSGHTPLHLAAYSGHLEIVEVLLKAGADVNA (SEQ ID NO:14).

5. The recombinant binding protein of claim 1, wherein said ankyrin repeat module has the amino acid sequence KDQEGTTPLHFAASVGHLEIVEVLLKAGADVNA (SEQ ID NO:15).

6. The recombinant binding protein of claim 1, wherein said ankyrin repeat module has the amino acid sequence KDQEGTTPLHFAASVGHLEIVEVLLKAGADVNA (SEQ ID NO:15), wherein up to 6 amino acids in SEQ ID NO:15 are exchanged by another amino acid, wherein the up to 6 amino acid exchanges are:
Q at position 3 is optionally exchanged by A;
E at position 4 is optionally exchanged by D;
T at position 6 is optionally exchanged by E;
F at position 11 is optionally exchanged by Y;
S at position 14 is optionally exchanged by V; and
V at position 15 is optionally exchanged by W.

7. The recombinant binding protein of claim 1, wherein said ankyrin repeat module has the amino acid sequence KDLNGQTPLHLAADIGHLEIVEVLLKAGADVNA (SEQ ID NO:17).

8. The recombinant binding protein of claim 1, wherein said ankyrin repeat module has the amino acid sequence KDLNGQTPLHLAADIGHLEIVEVLLKAGADVNA (SEQ ID NO:17), wherein up to 2 amino acids in SEQ ID NO:17 are exchanged by another amino acid, wherein the up to 2 amino acid exchanges are:
K at position 1 is optionally exchanged by Q or I; and
L at position 3 is optionally exchanged by N.

9. The recombinant binding protein of claim 1, wherein said ankyrin repeat module has the amino acid sequence KDYAGSTPLRLAAWAGHLEIVEVLLKAGADVNA (SEQ ID NO:18).

10. The recombinant binding protein of claim 1, wherein said ankyrin repeat module has the amino acid sequence KDYAGSTPLRLAAWAGHLEIVEVLLKAGADVNA (SEQ ID NO:18), wherein up to 3 amino acids in SEQ ID NO:18 are exchanged by another amino acid, wherein the up to 3 amino acid exchanges are:
K at position 1 is optionally exchanged by Q;
W at position 14 is optionally exchanged by H; and
A at position 15 is optionally exchanged by V.

11. The recombinant binding protein of claim 1, wherein said ankyrin repeat module has the amino acid sequence KDYFGYTPLHLAAYFGHLEIVEVLLKAGADVNA (SEQ ID NO:19).

12. The recombinant binding protein of claim 1, wherein said ankyrin repeat module has the amino acid sequence KDYFGYTPLHLAAYFGHLEIVEVLLKAGADVNA (SEQ ID NO:19), wherein up to 4 amino acids in SEQ ID NO:19 are exchanged by another amino acid, wherein the up to 4 amino acid exchanges are:
K at position 1 is optionally exchanged by N;
A at position 12 is optionally exchanged by T;
A at position 13 is optionally exchanged by T; and
E at position 22 is optionally exchanged by D.

13. A recombinant binding protein comprising at least one ankyrin repeat domain, wherein said ankyrin repeat domain specifically binds PDGF-BB and wherein said ankyrin repeat domain comprises an amino acid sequence that has at least 90% amino acid sequence identity with one ankyrin repeat domain selected from the group consisting of SEQ ID NOs: 23 to 60, wherein G at position 1 and/or S at position 2 of said ankyrin repeat domain are optionally missing, and L at the second last position and/or N at the last position of said ankyrin repeat domain are optionally exchanged by A.

14. The recombinant binding protein of claim 13, wherein said ankyrin repeat domain comprises an amino acid sequence that has at least 95% amino acid sequence identity with one ankyrin repeat domain selected from the group consisting of SEQ ID NOs: 23 to 60, wherein G at position 1 and/or S at position 2 of said ankyrin repeat domain are optionally missing, and L at the second last position and/or N at the last position of said ankyrin repeat domain are optionally exchanged by A.

15. A recombinant binding protein comprising at least one ankyrin repeat domain, wherein said ankyrin repeat domain specifically binds PDGF-BB and wherein said ankyrin repeat domain comprises an amino acid sequence that has at least 85% amino acid sequence identity with SEQ ID NO: 24, wherein G at position 1 and/or S at position 2 of said ankyrin repeat domain are optionally missing, and L at the second last position and/or N at the last position of said ankyrin repeat domain are optionally exchanged by A.

16. A recombinant binding protein comprising at least one ankyrin repeat domain, wherein said ankyrin repeat domain specifically binds PDGF-BB and wherein said ankyrin repeat domain comprises an amino acid sequence that has at least 85% amino acid sequence identity with SEQ ID NO: 45, wherein G at position 1 and/or S at position 2 of said ankyrin repeat domain are optionally missing, and L at the second last position and/or N at the last position of said ankyrin repeat domain are optionally exchanged by A.

17. A recombinant binding protein comprising at least one ankyrin repeat domain, wherein said ankyrin repeat domain specifically binds PDGF-BB and wherein said ankyrin repeat domain comprises an amino acid sequence that has at least 85% amino acid sequence identity with SEQ ID NO: 50, wherein G at position 1 and/or S at position 2 of said ankyrin repeat domain are optionally missing, and L at the second last position and/or N at the last position of said ankyrin repeat domain are optionally exchanged by A.

18. The recombinant binding protein of claim 1, wherein said ankyrin repeat domain binds PDGF-BB in PBS with a Kd below $10^{-7}$M.

19. The recombinant binding protein of claim 1, wherein said ankyrin repeat domain inhibits the binding of PDGF-BB to PDGFRbeta in PBS with an $IC_{50}$ value below $10^{-7}$M.

20. The recombinant binding protein of claim 1, wherein said ankyrin repeat domain inhibits the PDGF-BB stimulated proliferation of 3T3 fibroblasts with an $IC_{50}$ value below $10^{-7}$ M.

21. The binding protein of claim 1, wherein said ankyrin repeat domain comprises a capping module having an amino acid sequence selected from the group consisting of SEQ ID NO:13 and 16 and sequences, wherein up to 8 amino acids in SEQ ID NO:13 and 16 are exchanged by any amino acid.

22. A nucleic acid encoding a binding protein of claim 1.

23. A pharmaceutical composition comprising the binding protein of claim 1, and optionally a pharmaceutical acceptable carrier and/or diluent.

24. A pharmaceutical composition comprising the nucleic acid of claim 22, and optionally a pharmaceutical acceptable carrier and/or diluent.

25. A recombinant binding protein comprising at least one ankyrin repeat domain, wherein said ankyrin repeat domain binds PDGF-BB in PBS, wherein said ankyrin repeat domain is selected from the group consisting of SEQ ID NOs:23 to 60 wherein G at position 1 and/or S at position 2 of said ankyrin repeat domain are optionally missing; and L at the second last position and/or N at the last position of said ankyrin repeat domain are optionally exchanged by A.

26. A recombinant binding protein comprising at least one ankyrin repeat domain, wherein said ankyrin repeat domain binds PDGF-BB in PBS and comprises the ankyrin repeat module of SEQ ID NO:12 directly followed by the C-terminal capping module of SEQ ID NO:13.

27. A recombinant binding protein, comprising at least one ankyrin repeat domain, wherein said ankyrin repeat domain specifically binds PDGF-BB, and wherein said recombinant binding protein comprises a peptide of any one of the sequences SEQ ID NO:12 to 19 and 23 to 61.

* * * * *

SEQUENCE LISTING

<160> NUMBER OF SEQ ID NOS: 65

<210> SEQ ID NO 1
<211> LENGTH: 32
<212> TYPE: PRT
<213> ORGANISM: Artificial sequence
<220> FEATURE:
<223> OTHER INFORMATION: Synthetic construct

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

<210> SEQ ID NO 2
<211> LENGTH: 32
<212> TYPE: PRT
<213> ORGANISM: Artificial sequence
<220> FEATURE:
<223> OTHER INFORMATION: Synthetic construct

<400> SEQUENCE: 2

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

<210> SEQ ID NO 3
<211> LENGTH: 32
<212> TYPE: PRT
<213> ORGANISM: Artificial sequence
<220> FEATURE:
<223> OTHER INFORMATION: Synthetic construct

<400> SEQUENCE: 3

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

<210> SEQ ID NO 4
<211> LENGTH: 28
<212> TYPE: PRT
<213> ORGANISM: Artificial sequence
<220> FEATURE:
<223> OTHER INFORMATION: Synthetic construct

<400> SEQUENCE: 4

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
            20                  25

```
<210> SEQ ID NO 5
<211> LENGTH: 28
<212> TYPE: PRT
<213> ORGANISM: Artificial sequence
<220> FEATURE:
<223> OTHER INFORMATION: Synthetic construct

<400> SEQUENCE: 5

Gln Asp Lys Phe Gly Lys Thr Pro Phe Asp Leu Ala Ile Arg Glu Gly
1               5                   10                  15

His Glu Asp Ile Ala Glu Val Leu Gln Lys Ala Ala
            20                  25

<210> SEQ ID NO 6
<211> LENGTH: 28
<212> TYPE: PRT
<213> ORGANISM: Artificial sequence
<220> FEATURE:
<223> OTHER INFORMATION: Synthetic construct

<400> SEQUENCE: 6

Gln Asp Lys Phe Gly Lys Thr Pro Phe Asp Leu Ala Ile Asp Asn Gly
1               5                   10                  15

Asn Glu Asp Ile Ala Glu Val Leu Gln Lys Ala Ala
            20                  25

<210> SEQ ID NO 7
<211> LENGTH: 28
<212> TYPE: PRT
<213> ORGANISM: Artificial sequence
<220> FEATURE:
<223> OTHER INFORMATION: Synthetic construct

<400> SEQUENCE: 7

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 8
<211> LENGTH: 28
<212> TYPE: PRT
<213> ORGANISM: Artificial sequence
<220> FEATURE:
<223> OTHER INFORMATION: Synthetic construct

<400> SEQUENCE: 8

Gln Asp Lys Phe Gly Lys Thr Pro Ala Asp Ile Ala Ala Asp Asn Gly
1               5                   10                  15

His Glu Asp Ile Ala Glu Val Leu Gln Lys Leu Asn
            20                  25

<210> SEQ ID NO 9
<211> LENGTH: 10
<212> TYPE: PRT
<213> ORGANISM: Artificial sequence
<220> FEATURE:
<223> OTHER INFORMATION: Synthetic construct

<400> SEQUENCE: 9

Met Arg Gly Ser His His His His His His
1               5                   10

<210> SEQ ID NO 10
```

```
<211> LENGTH: 20
<212> TYPE: PRT
<213> ORGANISM: Artificial sequence
<220> FEATURE:
<223> OTHER INFORMATION: Synthetic construct

<400> SEQUENCE: 10

Gly Gly Gly Gly Ser Gly Gly Gly Ser Gly Gly Gly Ser Gly
1               5                   10                  15

Gly Gly Gly Ser
            20

<210> SEQ ID NO 11
<211> LENGTH: 20
<212> TYPE: PRT
<213> ORGANISM: Artificial sequence
<220> FEATURE:
<223> OTHER INFORMATION: Synthetic construct

<400> SEQUENCE: 11

Pro Thr Pro Thr Pro Thr Thr Pro Thr Pro Thr Pro Thr Thr Pro Thr
1               5                   10                  15

Pro Thr Pro Thr
            20

<210> SEQ ID NO 12
<211> LENGTH: 33
<212> TYPE: PRT
<213> ORGANISM: Artificial sequence
<220> FEATURE:
<223> OTHER INFORMATION: Synthetic construct

<400> SEQUENCE: 12

Lys Asp Glu Glu Gly Thr Thr Pro Leu His Tyr Ala Ala Val Trp Gly
1               5                   10                  15

His Leu Glu Ile Val Glu Val Leu Leu Lys Ala Gly Ala Asp Val Asn
            20                  25                  30

Ala

<210> SEQ ID NO 13
<211> LENGTH: 28
<212> TYPE: PRT
<213> ORGANISM: Artificial sequence
<220> FEATURE:
<223> OTHER INFORMATION: Synthetic construct

<400> SEQUENCE: 13

Gln Asp Ile Tyr Gly Ala Thr Pro Ala Asp Leu Ala Ala Leu Val Gly
1               5                   10                  15

His Glu Asp Ile Ala Glu Val Leu Gln Lys Leu Asn
            20                  25

<210> SEQ ID NO 14
<211> LENGTH: 33
<212> TYPE: PRT
<213> ORGANISM: Artificial sequence
<220> FEATURE:
<223> OTHER INFORMATION: Synthetic construct

<400> SEQUENCE: 14

Lys Asp Lys Ser Gly His Thr Pro Leu His Leu Ala Ala Tyr Ser Gly
1               5                   10                  15

His Leu Glu Ile Val Glu Val Leu Leu Lys Ala Gly Ala Asp Val Asn
            20                  25                  30
```

Ala

<210> SEQ ID NO 15
<211> LENGTH: 33
<212> TYPE: PRT
<213> ORGANISM: Artificial sequence
<220> FEATURE:
<223> OTHER INFORMATION: Synthetic construct

<400> SEQUENCE: 15

Lys Asp Gln Glu Gly Thr Thr Pro Leu His Phe Ala Ala Ser Val Gly
1               5                   10                  15

His Leu Glu Ile Val Glu Val Leu Leu Lys Ala Gly Ala Asp Val Asn
            20                  25                  30

Ala

<210> SEQ ID NO 16
<211> LENGTH: 28
<212> TYPE: PRT
<213> ORGANISM: Artificial sequence
<220> FEATURE:
<223> OTHER INFORMATION: Synthetic construct

<400> SEQUENCE: 16

Gln Asp His Tyr Gly Ala Thr Pro Ala Asp Leu Ala Ala Leu Ile Gly
1               5                   10                  15

His Glu Asp Ile Ala Glu Val Leu Gln Lys Leu Asn
            20                  25

<210> SEQ ID NO 17
<211> LENGTH: 33
<212> TYPE: PRT
<213> ORGANISM: Artificial sequence
<220> FEATURE:
<223> OTHER INFORMATION: Synthetic construct

<400> SEQUENCE: 17

Lys Asp Leu Asn Gly Gln Thr Pro Leu His Leu Ala Ala Asp Ile Gly
1               5                   10                  15

His Leu Glu Ile Val Glu Val Leu Leu Lys Ala Gly Ala Asp Val Asn
            20                  25                  30

Ala

<210> SEQ ID NO 18
<211> LENGTH: 33
<212> TYPE: PRT
<213> ORGANISM: Artificial sequence
<220> FEATURE:
<223> OTHER INFORMATION: Synthetic construct

<400> SEQUENCE: 18

Lys Asp Tyr Ala Gly Ser Thr Pro Leu Arg Leu Ala Ala Trp Ala Gly
1               5                   10                  15

His Leu Glu Ile Val Glu Val Leu Leu Lys Ala Gly Ala Asp Val Asn
            20                  25                  30

Ala

<210> SEQ ID NO 19
<211> LENGTH: 33
<212> TYPE: PRT
<213> ORGANISM: Artificial sequence
<220> FEATURE:

<223> OTHER INFORMATION: Synthetic construct

<400> SEQUENCE: 19

Lys Asp Tyr Phe Gly Tyr Thr Pro Leu His Leu Ala Ala Tyr Phe Gly
1               5                   10                  15

His Leu Glu Ile Val Glu Val Leu Leu Lys Ala Gly Ala Asp Val Asn
            20                  25                  30

Ala

<210> SEQ ID NO 20
<211> LENGTH: 33
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 20

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 21
<211> LENGTH: 159
<212> TYPE: PRT
<213> ORGANISM: Artificial sequence
<220> FEATURE:
<223> OTHER INFORMATION: Synthetic construct

<400> SEQUENCE: 21

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Asn Asp Gly Tyr Thr Pro Leu His Leu Ala Ala Ser Asn Gly
        35                  40                  45

His Leu Glu Ile Val Glu Val Leu Leu Lys Asn Gly Ala Asp Val Asn
    50                  55                  60

Ala Ser Asp Leu Thr Gly Ile Thr Pro Leu His Leu Ala Ala Ala Thr
65                  70                  75                  80

Gly His Leu Glu Ile Val Glu Val Leu Leu Lys His Gly Ala Asp Val
                85                  90                  95

Asn Ala Tyr Asp Asn Asp Gly His Thr Pro Leu His Leu Ala Ala Lys

```
                    100                 105                 110
Tyr Gly His Leu Glu Ile Val Glu Val Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Lys Leu Asn
145                 150                 155

<210> SEQ ID NO 22
<211> LENGTH: 126
<212> TYPE: PRT
<213> ORGANISM: Artificial sequence
<220> FEATURE:
<223> OTHER INFORMATION: Synthetic construct

<400> SEQUENCE: 22

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Lys Asp Gly Tyr Thr Pro Leu His Leu Ala Ala Arg Glu Gly
        35                  40                  45

His Leu Glu Ile Val Glu Val Leu Leu Lys Ala Gly Ala Asp Val Asn
    50                  55                  60

Ala Lys Asp Lys Asp Gly Tyr Thr Pro Leu His Leu Ala Ala Arg Glu
65                  70                  75                  80

Gly His Leu Glu Ile Val Glu Val Leu Leu Lys Ala Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Asn
            115                 120                 125

<210> SEQ ID NO 23
<211> LENGTH: 93
<212> TYPE: PRT
<213> ORGANISM: Artificial sequence
<220> FEATURE:
<223> OTHER INFORMATION: Synthetic construct

<400> SEQUENCE: 23

Gly Ser Asp Leu Gly Trp Lys Leu Leu Gln Ala Ala Lys Phe Gly Gln
1               5                   10                  15

Asp Asp Glu Val Arg Ile Leu Leu Ala Ala Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90

<210> SEQ ID NO 24
<211> LENGTH: 93
<212> TYPE: PRT
<213> ORGANISM: Artificial sequence
<220> FEATURE:
```

<223> OTHER INFORMATION: Synthetic construct

<400> SEQUENCE: 24

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90

<210> SEQ ID NO 25
<211> LENGTH: 93
<212> TYPE: PRT
<213> ORGANISM: Artificial sequence
<220> FEATURE:
<223> OTHER INFORMATION: Synthetic construct

<400> SEQUENCE: 25

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Ile Leu Gln Lys Leu Asn
                85                  90

<210> SEQ ID NO 26
<211> LENGTH: 93
<212> TYPE: PRT
<213> ORGANISM: Artificial sequence
<220> FEATURE:
<223> OTHER INFORMATION: Synthetic construct

<400> SEQUENCE: 26

Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Ile Leu Gln Lys Leu Asn
                85                  90

-continued

```
<210> SEQ ID NO 27
<211> LENGTH: 93
<212> TYPE: PRT
<213> ORGANISM: Artificial sequence
<220> FEATURE:
<223> OTHER INFORMATION: Synthetic construct

<400> SEQUENCE: 27

Gly Ser Asp Leu Gly Lys Lys Leu Leu Glu Ala Ala Arg Ala Gly Gln
1               5                   10                  15

Asp Asp Glu Val Arg Ile Leu Leu Ala Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90

<210> SEQ ID NO 28
<211> LENGTH: 93
<212> TYPE: PRT
<213> ORGANISM: Artificial sequence
<220> FEATURE:
<223> OTHER INFORMATION: Synthetic construct

<400> SEQUENCE: 28

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90

<210> SEQ ID NO 29
<211> LENGTH: 93
<212> TYPE: PRT
<213> ORGANISM: Artificial sequence
<220> FEATURE:
<223> OTHER INFORMATION: Synthetic construct

<400> SEQUENCE: 29

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Glu Glu Gly Thr Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80
```

```
Gly His Glu Asp Ile Ala Glu Val Leu Gln Lys Leu Asn
                85                  90
```

<210> SEQ ID NO 30
<211> LENGTH: 93
<212> TYPE: PRT
<213> ORGANISM: Artificial sequence
<220> FEATURE:
<223> OTHER INFORMATION: Synthetic construct

<400> SEQUENCE: 30

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Glu Glu Gly Thr Thr Pro Leu His Tyr Ala Ala Val Tyr Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90
```

<210> SEQ ID NO 31
<211> LENGTH: 93
<212> TYPE: PRT
<213> ORGANISM: Artificial sequence
<220> FEATURE:
<223> OTHER INFORMATION: Synthetic construct

<400> SEQUENCE: 31

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Glu Glu Gly Thr Thr Pro Leu His Tyr Ala Ala Val Phe Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Val
65                  70                  75                  80

Gly His Glu Asp Ile Ala Glu Val Leu Gln Lys Leu Asn
                85                  90
```

<210> SEQ ID NO 32
<211> LENGTH: 93
<212> TYPE: PRT
<213> ORGANISM: Artificial sequence
<220> FEATURE:
<223> OTHER INFORMATION: Synthetic construct

<400> SEQUENCE: 32

```
Gly Ser Asp Leu Gly His Lys Leu Leu Gln Ala Ala Lys His Gly Gln
1               5                   10                  15

Asp Asp Glu Val Arg Ile Leu Leu Ala Ala Gly Ala Asp Val Asn Ala
            20                  25                  30

Lys Asp Asp Glu Gly Thr Thr Pro Leu His Tyr Ala Ala Val Trp Gly
        35                  40                  45
```

-continued

His Leu Glu Ile Val Glu Val Leu Leu Lys Ala Gly Ala Asp Val Asn
        50                  55                  60

Ala Gln Asp Ala Tyr Gly Ala Thr Pro Ala Asp Leu Ala Phe Leu
65                  70                  75                  80

Gly His Glu Asp Ile Ala Glu Val Leu Gln Lys Leu Asn
                85                  90

<210> SEQ ID NO 33
<211> LENGTH: 93
<212> TYPE: PRT
<213> ORGANISM: Artificial sequence
<220> FEATURE:
<223> OTHER INFORMATION: Synthetic construct

<400> SEQUENCE: 33

Gly Ser Asp Leu Gly His Lys Leu Leu Gln Ala Ala Glu Gln Gly Gln
1               5                   10                  15

Asp Asp Glu Val Arg Ile Leu Leu Ala Ala Gly Ala Asp Val Asn Ala
                20                  25                  30

Lys Asp Glu Tyr Gly Thr Thr Pro Leu His Phe Ala Ala Val Trp Gly
            35                  40                  45

His Leu Glu Ile Val Glu Val Leu Leu Lys Ala Gly Ala Asp Val Asn
        50                  55                  60

Ala Gln Asp Val Phe Gly Ala Thr Pro Ala Asp Leu Ala Ala Tyr Val
65                  70                  75                  80

Gly His Glu Asp Ile Ala Glu Val Leu Gln Lys Leu Asn
                85                  90

<210> SEQ ID NO 34
<211> LENGTH: 102
<212> TYPE: PRT
<213> ORGANISM: Artificial sequence
<220> FEATURE:
<223> OTHER INFORMATION: Synthetic construct

<400> SEQUENCE: 34

Gly Ser Asp Leu Gly Asp Lys Leu Leu Gln Ser Asp Leu Gly Arg Lys
1               5                   10                  15

Leu Leu His Ala Ala Arg Ser Gly Gln Asp Asp Glu Val Arg Ile Leu
                20                  25                  30

Leu Ala Ala Gly Ala Asp Val Asn Ala Lys Asp Glu Asp Gly Thr Thr
            35                  40                  45

Pro Leu His Tyr Ala Ala Ala Trp Gly His Leu Glu Ile Val Glu Val
        50                  55                  60

Leu Leu Lys Ala Gly Ala Asp Val Asn Ala Gln Asp Ile Tyr Gly Ala
65                  70                  75                  80

Thr Pro Ala Asp Leu Ala Ala Tyr Ile Gly His Glu Asp Ile Ala Glu
                85                  90                  95

Val Leu Gln Lys Leu Asn
            100

<210> SEQ ID NO 35
<211> LENGTH: 93
<212> TYPE: PRT
<213> ORGANISM: Artificial sequence
<220> FEATURE:
<223> OTHER INFORMATION: Synthetic construct

<400> SEQUENCE: 35

Gly Ser Asp Leu Gly Gln Lys Leu Leu Tyr Ala Ala Glu His Gly Gln
1               5                   10                  15

```
1               5                   10                  15
Asp Asp Glu Val Arg Ile Leu Leu Ala Ala Gly Ala Asp Val Asn Ala
            20                  25                  30

Lys Asp Gln Thr Gly Ser Thr Pro Leu His Tyr Ala Ala Val Trp Gly
        35                  40                  45

His Met Glu Ile Val Glu Val Leu Leu Lys Ala Gly Ala Asp Val Asn
    50                  55                  60

Ala Gln Asp Leu Trp Gly Ala Thr Pro Ala Asp Leu Ala Ala Phe Leu
65                  70                  75                  80

Gly His Glu Asp Ile Ala Val Val Leu Gln Lys Leu Asn
                85                  90
```

<210> SEQ ID NO 36
<211> LENGTH: 93
<212> TYPE: PRT
<213> ORGANISM: Artificial sequence
<220> FEATURE:
<223> OTHER INFORMATION: Synthetic construct

<400> SEQUENCE: 36

```
Gly Ser Asp Leu Gly Ser Lys Leu Leu Thr Ala Ala Leu Asp Gly Gln
1               5                   10                  15

Asp Asp Glu Val Arg Ile Leu Leu Ala Ala Gly Ala Asp Val Asn Ala
            20                  25                  30

Lys Asp Glu Gly Thr Thr Pro Leu His Tyr Ala Ala Val Val Gly
        35                  40                  45

His Leu Glu Ile Val Glu Val Leu Leu Lys Ala Gly Ala Asp Val Asn
    50                  55                  60

Ala Gln Asp Ile Trp Gly Ala Thr Pro Ala Asp Leu Ala Ala Leu Val
65                  70                  75                  80

Gly His Glu Asp Ile Ala Glu Val Leu Gln Lys Leu Asn
                85                  90
```

<210> SEQ ID NO 37
<211> LENGTH: 93
<212> TYPE: PRT
<213> ORGANISM: Artificial sequence
<220> FEATURE:
<223> OTHER INFORMATION: Synthetic construct

<400> SEQUENCE: 37

```
Gly Ser Asp Leu Gly Trp Lys Leu Leu Glu Ala Ala Arg Thr Gly Gln
1               5                   10                  15

Asp Asp Glu Val Arg Ile Leu Leu Ala Ala Gly Ala Asp Val Asn Ala
            20                  25                  30

Lys Asp Ile Thr Gly Thr Thr Pro Leu His Tyr Ala Ala Ala Trp Gly
        35                  40                  45

His Met Glu Ile Val Glu Val Leu Leu Lys Thr Gly Ala Asp Val Asn
    50                  55                  60

Ala Gln Asp Leu Tyr Gly Ala Thr Pro Ala Asp Leu Ala Ala Leu Leu
65                  70                  75                  80

Gly His Glu Asp Ile Ala Glu Val Leu Gln Lys Leu Asn
                85                  90
```

<210> SEQ ID NO 38
<211> LENGTH: 93
<212> TYPE: PRT
<213> ORGANISM: Artificial sequence
<220> FEATURE:

<223> OTHER INFORMATION: Synthetic construct

<400> SEQUENCE: 38

Gly Ser Asp Leu Gly Asp Lys Leu Leu Trp Ala Ala Lys His Gly Gln
1               5                   10                  15

Asp Asp Glu Val Arg Ile Leu Leu Ala Ala Gly Ala Asp Val Asn Ala
            20                  25                  30

Lys Asp Asp Glu Gly Ser Thr Pro Leu His Tyr Ala Ala Val Trp Gly
        35                  40                  45

His Leu Glu Thr Val Glu Val Leu Leu Lys Ala Gly Ala Asp Val Asn
    50                  55                  60

Ala Gln Asp Ile Trp Gly Ala Thr Pro Ala Asp Leu Ala Ala Leu Leu
65                  70                  75                  80

Gly His Glu Asp Ile Ala Glu Val Leu Gln Lys Leu Asn
                85                  90

<210> SEQ ID NO 39
<211> LENGTH: 93
<212> TYPE: PRT
<213> ORGANISM: Artificial sequence
<220> FEATURE:
<223> OTHER INFORMATION: Synthetic construct

<400> SEQUENCE: 39

Gly Ser Asp Leu Gly Asn Lys Leu Leu Ser Ala Ala Arg Leu Gly Gln
1               5                   10                  15

Asp Asp Glu Val Arg Ile Leu Leu Ala Ala Gly Ala Asp Val Asn Ala
            20                  25                  30

Lys Asp Trp Asp Gly Ser Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Leu Tyr Gly Ala Thr Pro Ala Asp Leu Ala Ala Leu Ile
65                  70                  75                  80

Gly His Glu Asp Ile Ala Glu Val Leu Gln Lys Leu Asn
                85                  90

<210> SEQ ID NO 40
<211> LENGTH: 93
<212> TYPE: PRT
<213> ORGANISM: Artificial sequence
<220> FEATURE:
<223> OTHER INFORMATION: Synthetic construct

<400> SEQUENCE: 40

Gly Ser Asp Leu Gly Tyr Lys Leu Leu Ser Ala Ala Gln Tyr Gly Gln
1               5                   10                  15

Asp Asp Glu Val Arg Ile Leu Leu Ala Ala Gly Ala Asp Val Asn Ala
            20                  25                  30

Lys Asp Tyr Ser Gly Thr Thr Pro Leu His Tyr Ala Ala Thr Trp Gly
        35                  40                  45

His Leu Glu Ile Val Glu Val Leu Leu Lys Ala Gly Ala Asp Val Asn
    50                  55                  60

Ala Gln Asp Ile Tyr Gly Ala Thr Pro Ala Asp Leu Ala Ala Leu Ile
65                  70                  75                  80

Gly His Glu Asp Ile Ala Glu Val Leu Gln Lys Leu Asn
                85                  90

```
<210> SEQ ID NO 41
<211> LENGTH: 93
<212> TYPE: PRT
<213> ORGANISM: Artificial sequence
<220> FEATURE:
<223> OTHER INFORMATION: Synthetic construct

<400> SEQUENCE: 41

Gly Ser Asp Leu Gly Arg Lys Leu Leu Tyr Ala Ala Trp Ala Gly Gln
1               5                   10                  15

Asp Asp Glu Val Arg Ile Leu Leu Ala Ala Gly Val Asp Val Asn Ala
            20                  25                  30

Lys Asp Trp Thr Gly Phe Thr Pro Leu His Tyr Ala Ala Tyr Lys Gly
        35                  40                  45

His Leu Glu Ile Val Glu Val Leu Leu Lys Ala Gly Ala Asp Val Asn
    50                  55                  60

Ala Gln Asp Ala Trp Gly Ala Thr Pro Ala Asp Leu Ala Ala Phe Val
65                  70                  75                  80

Gly His Glu Asp Ile Ala Glu Val Leu Gln Lys Leu Asn
                85                  90

<210> SEQ ID NO 42
<211> LENGTH: 127
<212> TYPE: PRT
<213> ORGANISM: Artificial sequence
<220> FEATURE:
<223> OTHER INFORMATION: Synthetic construct

<400> SEQUENCE: 42

Gly Ser Asp Leu Gly Tyr Lys Leu Leu Phe Ala Ala Tyr Val Gly Gln
1               5                   10                  15

Asp Asp Glu Val Arg Ile Leu Leu Ala Ala Gly Ala Asp Val Asn Ala
            20                  25                  30

Lys Asp Arg His Gly Arg Thr Pro Leu His Leu Ala Ala Trp Glu Gly
        35                  40                  45

His Leu Glu Ile Val Glu Val Leu Leu Lys Ala Gly Ala Asp Val Asn
    50                  55                  60

Ala Lys Asp Asp Glu Gly Thr Thr Pro Leu His Leu Leu Ala Ala Trp
65                  70                  75                  80

Glu Gly His Leu Glu Ile Val Glu Val Leu Leu Lys Ala Gly Ala Asp
                85                  90                  95

Val Asn Ala Gln Asp Val Tyr Gly Ala Thr Pro Ala Asp Leu Ala Ala
            100                 105                 110

Tyr Ile Gly His Glu Asp Ile Ala Glu Val Leu Gln Lys Leu Asn
        115                 120                 125

<210> SEQ ID NO 43
<211> LENGTH: 126
<212> TYPE: PRT
<213> ORGANISM: Artificial sequence
<220> FEATURE:
<223> OTHER INFORMATION: Synthetic construct

<400> SEQUENCE: 43

Gly Ser Asp Leu Gly Leu Lys Leu Leu Glu Ala Ala Gln Arg Gly Gln
1               5                   10                  15

Asp Asp Glu Val Arg Ile Leu Leu Ala Ala Gly Ala Asp Val Asn Ala
            20                  25                  30

Lys Asp Arg Glu Gly Trp Thr Pro Leu His Val Ala Ala Tyr Glu Gly
        35                  40                  45
```

```
His Leu Glu Ile Val Glu Val Leu Lys Ala Gly Ala Asp Val Asn
    50                  55                  60

Ala Lys Asp Tyr Thr Gly Leu Thr Pro Leu His Val Ala Ala Val Trp
65                  70                  75                  80

Gly His Leu Glu Ile Val Glu Val Leu Lys Ala Gly Ala Asp Val
                85                  90                  95

Asn Ala Gln Asp Ile Tyr Gly Ala Thr Pro Ala Asp Leu Ala Ala Tyr
                100                 105                 110

Ile Gly His Glu Asp Ile Ala Glu Val Leu Gln Lys Leu Asn
        115                 120                 125
```

<210> SEQ ID NO 44
<211> LENGTH: 126
<212> TYPE: PRT
<213> ORGANISM: Artificial sequence
<220> FEATURE:
<223> OTHER INFORMATION: Synthetic construct

<400> SEQUENCE: 44

```
Gly Ser Asp Leu Gly Ala Lys Leu Leu His Ala Ala Val Val Gly Gln
1               5                   10                  15

Asp Asp Glu Val Arg Ile Leu Ala Ala Gly Ala Asp Val Asn Ala
                20                  25                  30

Lys Asp Lys Ser Gly His Thr Pro Leu His Leu Ala Ala Tyr Ser Gly
            35                  40                  45

His Leu Glu Ile Val Glu Val Leu Lys Ala Gly Ala Asp Val Asn
    50                  55                  60

Ala Lys Asp Gln Glu Gly Thr Thr Pro Leu His Phe Ala Ala Ser Val
65                  70                  75                  80

Gly His Leu Glu Ile Val Glu Val Leu Lys Ala Gly Ala Asp Val
                85                  90                  95

Asn Ala Gln Asp His Tyr Gly Ala Thr Pro Ala Asp Leu Ala Ala Leu
                100                 105                 110

Ile Gly His Glu Asp Ile Ala Glu Val Leu Gln Lys Leu Asn
        115                 120                 125
```

<210> SEQ ID NO 45
<211> LENGTH: 126
<212> TYPE: PRT
<213> ORGANISM: Artificial sequence
<220> FEATURE:
<223> OTHER INFORMATION: Synthetic construct

<400> SEQUENCE: 45

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Lys Ser Gly His Thr Pro Leu His Leu Ala Ala Tyr Ser Gly
            35                  40                  45

His Leu Glu Ile Val Glu Val Leu Lys Ala Gly Ala Asp Val Asn
    50                  55                  60

Ala Lys Asp Gln Glu Gly Thr Thr Pro Leu His Phe Ala Ala Ser Val
65                  70                  75                  80

Gly His Leu Glu Ile Val Glu Val Leu Lys Ala Gly Ala Asp Val
                85                  90                  95

Asn Ala Gln Asp His Tyr Gly Ala Thr Pro Ala Asp Leu Ala Ala Leu
```

```
            100                 105                 110

Ile Gly His Glu Asp Ile Ala Glu Val Leu Gln Lys Leu Asn
        115                 120                 125

<210> SEQ ID NO 46
<211> LENGTH: 126
<212> TYPE: PRT
<213> ORGANISM: Artificial sequence
<220> FEATURE:
<223> OTHER INFORMATION: Synthetic construct

<400> SEQUENCE: 46

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Lys Ser Gly His Thr Pro Leu His Leu Ala Ala Tyr Ser Gly
        35                  40                  45

His Leu Glu Ile Val Glu Val Leu Leu Lys Ala Gly Ala Asp Val Asn
    50                  55                  60

Ala Lys Asp Gln Glu Gly Thr Thr Pro Leu His Phe Ala Ala Ser Val
65                  70                  75                  80

Gly His Leu Glu Ile Val Glu Val Leu Leu Lys Ala Gly Ala Asp Val
                85                  90                  95

Asn Ala Gln Asp His Tyr Gly Ala Thr Pro Ala Asp Leu Ala Ala Leu
            100                 105                 110

Ile Gly His Glu Asp Ile Ala Glu Val Leu Gln Lys Leu Asn
        115                 120                 125

<210> SEQ ID NO 47
<211> LENGTH: 126
<212> TYPE: PRT
<213> ORGANISM: Artificial sequence
<220> FEATURE:
<223> OTHER INFORMATION: Synthetic construct

<400> SEQUENCE: 47

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Lys Ser Gly His Thr Pro Leu His Leu Ala Ala Tyr Ser Gly
        35                  40                  45

His Leu Glu Ile Val Glu Val Leu Leu Lys Ala Gly Ala Asp Val Asn
    50                  55                  60

Ala Lys Asp Gln Glu Gly Thr Thr Pro Leu His Phe Ala Ala Ser Val
65                  70                  75                  80

Gly His Leu Glu Ile Val Glu Val Leu Leu Lys Ala Gly Ala Asp Val
                85                  90                  95

Asn Ala Gln Asp His Tyr Gly Ala Thr Pro Ala Asp Leu Ala Ala Leu
            100                 105                 110

Ile Gly His Glu Asp Ile Ala Glu Val Leu Gln Lys Leu Asn
        115                 120                 125

<210> SEQ ID NO 48
<211> LENGTH: 93
<212> TYPE: PRT
<213> ORGANISM: Artificial sequence
<220> FEATURE:
```

<223> OTHER INFORMATION: Synthetic construct

<400> SEQUENCE: 48

Gly Ser Asp Leu Gly Gln Lys Leu Leu Val Ala Ala Lys Glu Gly Gln
1               5                   10                  15

Asp Asp Glu Val Arg Ile Leu Ala Ala Gly Ala Asp Val Asn Ala
            20                  25                  30

Lys Asp Ala Asp Gly Glu Thr Pro Leu His Tyr Ala Ala Val Trp Gly
        35                  40                  45

His Leu Glu Ile Val Glu Val Leu Leu Lys Ala Gly Ala Asp Val Asn
    50                  55                  60

Ala Gln Asp Ile Trp Gly Ala Thr Pro Ala Asp Leu Ala Ala Leu Ile
65                  70                  75                  80

Gly His Glu Asp Ile Ala Glu Val Leu Gln Lys Leu Asn
                85                  90

<210> SEQ ID NO 49
<211> LENGTH: 159
<212> TYPE: PRT
<213> ORGANISM: Artificial sequence
<220> FEATURE:
<223> OTHER INFORMATION: Synthetic construct

<400> SEQUENCE: 49

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Gln Asp Leu Asn Gly Gln Thr Pro Leu His Leu Ala Ala Asp Ile Gly
        35                  40                  45

His Leu Glu Ile Val Glu Val Leu Leu Lys His Gly Ala Asp Val Asn
    50                  55                  60

Ala Gln Asp Tyr Ala Gly Ser Thr Pro Leu Arg Leu Ala Ala Trp Ala
65                  70                  75                  80

Gly His Leu Glu Ile Val Glu Val Leu Leu Lys Asn Gly Ala Asp Val
                85                  90                  95

Asn Ala Asn Asp Tyr Phe Gly Tyr Thr Pro Leu His Leu Ala Ala Tyr
                100                 105                 110

Phe Gly His Leu Glu Ile Val Asp Val Leu Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Lys Leu Asn
145                 150                 155

<210> SEQ ID NO 50
<211> LENGTH: 159
<212> TYPE: PRT
<213> ORGANISM: Artificial sequence
<220> FEATURE:
<223> OTHER INFORMATION: Synthetic construct

<400> SEQUENCE: 50

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Leu Asn Gly Gln Thr Pro Leu His Leu Ala Ala Asp Ile Gly

```
            35                  40                  45
His Leu Glu Ile Val Glu Val Leu Leu Lys Ala Gly Ala Asp Val Asn
 50                  55                  60

Ala Lys Asp Tyr Ala Gly Ser Thr Pro Leu Arg Leu Ala Ala Trp Ala
 65                  70                  75                  80

Gly His Leu Glu Ile Val Glu Val Leu Leu Lys Ala Gly Ala Asp Val
                 85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
                115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Asn
145                 150                 155

<210> SEQ ID NO 51
<211> LENGTH: 159
<212> TYPE: PRT
<213> ORGANISM: Artificial sequence
<220> FEATURE:
<223> OTHER INFORMATION: Synthetic construct

<400> SEQUENCE: 51

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Lys Asp Leu Asn Gly Gln Thr Pro Leu His Leu Ala Ala Asp Ile Gly
                 35                  40                  45

His Leu Glu Ile Val Glu Val Leu Leu Lys Ala Gly Ala Asp Val Asn
 50                  55                  60

Ala Lys Asp Tyr Ala Gly Ser Thr Pro Leu Arg Leu Ala Ala Trp Ala
 65                  70                  75                  80

Gly His Leu Glu Ile Val Glu Val Leu Leu Lys Ala Gly Ala Asp Val
                 85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
                115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Asn
145                 150                 155

<210> SEQ ID NO 52
<211> LENGTH: 159
<212> TYPE: PRT
<213> ORGANISM: Artificial sequence
<220> FEATURE:
<223> OTHER INFORMATION: Synthetic construct

<400> SEQUENCE: 52

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30
```

Gln Asp Leu Asn Gly Gln Thr Pro Leu His Leu Ala Ala Asp Ile Gly
            35                  40                  45

His Leu Glu Ile Val Glu Val Leu Leu Lys His Gly Ala Asp Val Asn
         50                  55                  60

Ala Gln Asp Tyr Ala Gly Ser Thr Pro Leu Arg Leu Ala Ala Trp Ala
65                  70                  75                  80

Gly His Leu Glu Ile Val Glu Val Leu Leu Lys Asn Gly Ala Asp Val
             85                  90                  95

Asn Ala Asn Asp Tyr Phe Gly Tyr Thr Pro Leu His Leu Ala Ala Tyr
                100                 105                 110

Phe Gly His Leu Glu Ile Val Asp Val Leu Leu Lys His Gly Ala Asp
            115                 120                 125

Val Asn Ala Gln Asp Lys Phe Gly Lys Thr Pro Ala Asp Ile Ala Ala
        130                 135                 140

Asp Asn Gly His Glu Asp Ile Ala Glu Val Leu Gln Lys Leu Asn
145                 150                 155

<210> SEQ ID NO 53
<211> LENGTH: 159
<212> TYPE: PRT
<213> ORGANISM: Artificial sequence
<220> FEATURE:
<223> OTHER INFORMATION: Synthetic construct

<400> SEQUENCE: 53

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Leu Asn Gly Gln Thr Pro Leu His Leu Ala Ala Asp Ile Gly
        35                  40                  45

His Leu Glu Ile Val Glu Val Leu Leu Lys Ala Gly Ala Asp Val Asn
     50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Leu Lys Ala Gly Ala Asp Val
             85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
            115                 120                 125

Val Asn Ala Gln Asp Lys Phe Gly Lys Thr Pro Ala Asp Ile Ala Ala
        130                 135                 140

Asp Asn Gly His Glu Asp Ile Ala Glu Val Leu Gln Lys Leu Asn
145                 150                 155

<210> SEQ ID NO 54
<211> LENGTH: 159
<212> TYPE: PRT
<213> ORGANISM: Artificial sequence
<220> FEATURE:
<223> OTHER INFORMATION: Synthetic construct

<400> SEQUENCE: 54

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

```
Lys Asp Leu Asn Gly Gln Thr Pro Leu His Leu Ala Ala Asp Ile Gly
        35                  40                  45

His Leu Glu Ile Val Glu Val Leu Leu Lys Ala Gly Ala Asp Val Asn
    50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Leu Lys Ala Gly Ala Asp Val
                85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
            115                 120                 125

Val Asn Ala Gln Asp Lys Ser Gly Lys Thr Pro Ala Asp Leu Ala Ala
        130                 135                 140

Asp Ala Gly His Glu Asp Ile Ala Glu Val Leu Gln Lys Leu Asn
145                 150                 155

<210> SEQ ID NO 55
<211> LENGTH: 159
<212> TYPE: PRT
<213> ORGANISM: Artificial sequence
<220> FEATURE:
<223> OTHER INFORMATION: Synthetic construct

<400> SEQUENCE: 55

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Leu Asn Gly Gln Thr Pro Leu His Leu Ala Ala Asp Ile Gly
        35                  40                  45

His Leu Glu Ile Val Glu Val Leu Leu Lys Ala Gly Ala Asp Val Asn
    50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Leu Lys Ala Gly Ala Asp Val
                85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Lys Leu Asn
145                 150                 155

<210> SEQ ID NO 56
<211> LENGTH: 159
<212> TYPE: PRT
<213> ORGANISM: Artificial sequence
<220> FEATURE:
<223> OTHER INFORMATION: Synthetic construct

<400> SEQUENCE: 56

Gly Ser Asp Leu Asp Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30
```

```
            20                  25                  30
Lys Asp Leu Asn Gly Gln Thr Pro Leu His Leu Ala Ala Asp Ile Gly
        35                  40                  45

His Leu Glu Ile Val Glu Val Leu Lys Ala Gly Ala Asp Val Asn
    50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Lys Ala Gly Ala Asp Val
                85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Lys Ala Gly Ala Asp
            115                 120                 125

Val Asn Ala Gln Asp Lys Phe Gly Lys Thr Pro Ala Asp Ile Ala Ala
        130                 135                 140

Asp Asn Gly His Glu Asp Ile Ala Glu Val Leu Gln Lys Leu Asn
145                 150                 155

<210> SEQ ID NO 57
<211> LENGTH: 159
<212> TYPE: PRT
<213> ORGANISM: Artificial sequence
<220> FEATURE:
<223> OTHER INFORMATION: Synthetic construct

<400> SEQUENCE: 57

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Leu Asn Gly Gln Thr Pro Leu His Leu Ala Ala Asp Ile Gly
        35                  40                  45

His Leu Glu Ile Val Glu Val Leu Leu Lys Ala Gly Ala Asp Val Asn
    50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Leu Lys Ala Gly Ala Asp Val
                85                  90                  95

Asn Ala Lys Asp Tyr Phe Gly Tyr Thr Pro Leu His Leu Ala Ala Tyr
                100                 105                 110

Phe Gly His Leu Glu Ile Val Glu Val Leu Leu Lys Ala Gly Ala Asp
            115                 120                 125

Val Asn Ala Gln Asp Lys Ser Gly Lys Thr Pro Ala Asp Leu Ala Ala
        130                 135                 140

Asp Ala Gly His Glu Asp Ile Ala Glu Val Leu Gln Lys Leu Asn
145                 150                 155

<210> SEQ ID NO 58
<211> LENGTH: 159
<212> TYPE: PRT
<213> ORGANISM: Artificial sequence
<220> FEATURE:
<223> OTHER INFORMATION: Synthetic construct

<400> SEQUENCE: 58

Gly Ser Asp Leu Gly Lys Lys Leu Leu Glu Ala Ala Arg Ala Gly Gln
1               5                   10                  15
```

Asp Asp Glu Val Arg Glu Leu Leu Lys Ala Gly Ala Asp Val Asn Ala
            20                  25                  30

Lys Asp Leu Asn Gly Gln Thr Pro Leu His Leu Ala Ala Asp Ile Gly
        35                  40                  45

His Leu Glu Ile Val Glu Val Leu Leu Lys Ala Gly Ala Asp Val Asn
    50                  55                  60

Ala Lys Asp Tyr Ala Gly Ser Thr Pro Leu Arg Leu Ala Ala Trp Ala
65                  70                  75                  80

Gly His Leu Glu Ile Val Glu Val Leu Leu Lys Ala Gly Ala Asp Val
                85                  90                  95

Asn Ala Lys Asp Tyr Phe Gly Tyr Thr Pro Leu His Leu Ala Ala Tyr
            100                 105                 110

Phe Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Asp Ala Gly His Glu Asp Ile Ala Glu Val Leu Gln Lys Leu Asn
145                 150                 155

<210> SEQ ID NO 59
<211> LENGTH: 159
<212> TYPE: PRT
<213> ORGANISM: Artificial sequence
<220> FEATURE:
<223> OTHER INFORMATION: Synthetic construct

<400> SEQUENCE: 59

Gly Ser Asp Leu Gly Lys Lys Leu Leu Glu Ala Ala Arg Ala Gly Gln
1               5                   10                  15

Gly Asp Glu Val His Ile Leu Met Ala Asn Gly Ala Asp Val Asn Ala
            20                  25                  30

Gln Asp Leu Asn Gly Gln Thr Pro Leu His Leu Ala Ala Asp Ile Gly
        35                  40                  45

His Leu Glu Ile Val Glu Val Leu Leu Lys His Gly Ala Asp Val Asn
    50                  55                  60

Ala Gln Asp Tyr Ala Gly Ser Thr Pro Leu Arg Leu Ala Ala Trp Ala
65                  70                  75                  80

Gly His Leu Glu Ile Val Glu Val Leu Leu Lys Asn Gly Ala Asp Val
                85                  90                  95

Asn Ala Asn Asp Tyr Phe Gly Tyr Thr Pro Leu His Leu Ala Ala Tyr
            100                 105                 110

Phe Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 60
<211> LENGTH: 159
<212> TYPE: PRT
<213> ORGANISM: Artificial sequence
<220> FEATURE:
<223> OTHER INFORMATION: Synthetic construct

<400> SEQUENCE: 60

Gly Ser Asp Leu Gly Lys Lys Leu Leu Glu Ala Ala Arg Ala Gly Gln
1               5                   10                  15

```
Asp Asp Glu Val His Ile Leu Met Ala Asn Gly Ala Asp Val Asn Ala
            20                  25                  30

Ile Asp Asn Asn Gly Gln Thr Pro Leu His Leu Ala Ala Asp Ile Gly
        35                  40                  45

His Leu Glu Ile Val Glu Val Leu Leu Lys His Gly Ala Asp Val Asn
 50                  55                  60

Ala Gln Asp Tyr Ala Gly Ser Thr Pro Leu Arg Leu Ala Ala His Val
 65                  70                  75                  80

Gly His Leu Glu Ile Val Glu Val Leu Leu Lys Tyr Gly Ala Asp Val
                85                  90                  95

Asn Ala Asn Asp Tyr Phe Gly Phe Thr Pro Leu His Leu Thr Thr Tyr
            100                 105                 110

Phe Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

```
<210> SEQ ID NO 61
<211> LENGTH: 167
<212> TYPE: PRT
<213> ORGANISM: Artificial sequence
<220> FEATURE:
<223> OTHER INFORMATION: Synthetic construct

<400> SEQUENCE: 61
```

```
Gly Ser Asp Leu Gly Lys Lys Leu Leu Glu Ala Ala Arg Ala Gly Gln
 1               5                   10                  15

Asp Asp Glu Val Arg Ile Leu Met Ala Asn Gly Ala Asp Val Asn Ala
            20                  25                  30

Gln Asp Leu Asn Gly Gln Thr Pro Leu His Leu Ala Ala Asp Ile Gly
        35                  40                  45

His Leu Glu Ile Val Glu Val Leu Leu Lys His Gly Ala Asp Val Asn
 50                  55                  60

Ala Gln Asp Tyr Ala Gly Ser Thr Pro Leu Arg Leu Ala Ala Trp Ala
 65                  70                  75                  80

Gly His Leu Glu Ile Val Glu Val Leu Leu Lys Asn Gly Ala Asp Val
                85                  90                  95

Asn Ala Asn Asp Tyr Phe Gly Tyr Thr Pro Leu His Leu Ala Ala Tyr
            100                 105                 110

Phe Gly His Leu Glu Ile Val Asp Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Gly Gly
145                 150                 155                 160

Gly Ser Gly Gly Gly Ser Cys
                165
```

```
<210> SEQ ID NO 62
<211> LENGTH: 33
<212> TYPE: PRT
<213> ORGANISM: Artificial sequence
<220> FEATURE:
<223> OTHER INFORMATION: Synthetic construct
<220> FEATURE:
```

```
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 62

Lys Asp Xaa Xaa Gly Xaa Thr Pro Leu His Leu Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 63
<211> LENGTH: 33
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 63

Lys Asp Xaa Xaa Gly Xaa Thr Pro Leu His Xaa Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 64
<211> LENGTH: 32
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 64

Gly Ser Asp Leu Gly Xaa Lys Leu Leu Xaa Ala Ala Xaa Xaa Gly Gln
```

```
1               5                  10                 15
Asp Asp Glu Val Arg Ile Leu Leu Ala Ala Gly Ala Asp Val Asn Ala
            20                 25                 30

<210> SEQ ID NO 65
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 65

Gln Asp Xaa Xaa Gly Xaa Thr Pro Ala Asp Leu Ala Ala Xaa Xaa Gly
1               5                  10                 15

His Glu Asp Ile Ala Glu Val Leu Gln Lys Leu Asn
            20                 25
```